United States Patent
Haefeli

(10) Patent No.: US 11,778,397 B2
(45) Date of Patent: Oct. 3, 2023

(54) DEVICE FOR PROVIDING AN AUDIO SIGNAL

(71) Applicant: MY TINNITUS HAS GONE AG, Zürich (CH)

(72) Inventor: Oliver Haefeli, Zumikon (CH)

(73) Assignee: MY TINNITUS HAS GONE AG, Zürich (CH)

( * ) Notice: Subject to any disclaimer, the term of this patent is extended or adjusted under 35 U.S.C. 154(b) by 220 days.

(21) Appl. No.: 17/416,154

(22) PCT Filed: Dec. 20, 2019

(86) PCT No.: PCT/EP2019/086814
§ 371 (c)(1),
(2) Date: Jun. 18, 2021

(87) PCT Pub. No.: WO2020/128053
PCT Pub. Date: Jun. 25, 2020

(65) Prior Publication Data
US 2022/0078566 A1   Mar. 10, 2022

(30) Foreign Application Priority Data
Dec. 21, 2018   (CH) ........................... 1600/18

(51) Int. Cl.
*H04R 29/00* (2006.01)
*H04R 25/00* (2006.01)
(52) U.S. Cl.
CPC .................... *H04R 25/75* (2013.01)
(58) Field of Classification Search
CPC ................ H04R 3/007; H04R 29/00

USPC ................ 381/55–56, 58–60, 98, 320
See application file for complete search history.

(56) References Cited

U.S. PATENT DOCUMENTS

| | | |
|---|---|---|
| 6,047,074 A | 4/2000 | Zoels et al. |
| 9,020,621 B1 | 4/2015 | Proctor et al. |
| 9,277,337 B2 | 3/2016 | Haefeli |
| 9,549,269 B2 | 1/2017 | Notzel et al. |
| 2004/0141624 A1 | 7/2004 | Davis et al. |

(Continued)

FOREIGN PATENT DOCUMENTS

| | | |
|---|---|---|
| DE | 102007046020 A1 | 4/2009 |
| EP | 1559370 A2 | 8/2008 |

(Continued)

OTHER PUBLICATIONS

Patrick Neff, et al., "10 Hz Amplitude Modulated Sounds Induce Short-Term Tinnitus Suppression, Frontiers in Aging Neuroscience", May 19, 2017, vol. 9, Article 130, (11 pages).

(Continued)

*Primary Examiner* — George C Monikang
(74) *Attorney, Agent, or Firm* — Mannava & Kang, P.C.

(57) ABSTRACT

The present idea refers to a device for providing an audio signal for suppressing or decreasing a user's tinnitus. The device comprises an identification unit for supporting a determination of at least one parameter regarding the user's tinnitus, an adaptation unit configured to modify a received audio signal based on the at least one parameter, thereby obtaining the audio signal, or to generate the audio signal based on the at least one parameter, wherein a defined frequency spectrum of the audio signal is based on a tinnitus suppression frequency, and an audio output unit configured to play the audio signal to the user.

14 Claims, 21 Drawing Sheets

(56) References Cited

U.S. PATENT DOCUMENTS

| | | |
|---|---|---|
| 2005/0260985 A1 | 11/2005 | Rader et al. |
| 2007/0133832 A1 | 6/2007 | DiGiovanni et al. |
| 2009/0287492 A1 | 11/2009 | Chalupper et al. |
| 2010/0158262 A1 | 6/2010 | Schumaier et al. |
| 2010/0208631 A1 | 8/2010 | Zhang et al. |
| 2011/0071340 A1 | 3/2011 | McGuire |
| 2012/0046713 A1 | 2/2012 | Hannemann et al. |
| 2013/0039517 A1 | 2/2013 | Nielsen et al. |
| 2014/0288685 A1 | 9/2014 | Haefeli |

FOREIGN PATENT DOCUMENTS

| | | |
|---|---|---|
| WO | 0056120 A1 | 9/2000 |
| WO | 0170110 A1 | 9/2001 |
| WO | 2006130909 A1 | 12/2006 |
| WO | 2008087157 A2 | 7/2008 |
| WO | 2009061520 A1 | 5/2009 |
| WO | 2009119941 A1 | 10/2009 |
| WO | 2010040184 A1 | 4/2010 |
| WO | 2011116407 A1 | 9/2011 |
| WO | 2011127930 A1 | 10/2011 |

OTHER PUBLICATIONS

Magdalena Sereda, et al., "Re-examining the relationship between audiometric profile and tinnitus pitch", International Journal of Audiology, 2011, 50: 303-312, (11 pages).

Forum discussion about "Notched Music Therapy for Tinnitus—A Do it Your Self Video Guide", http://tinnitussupport92262.vuku.com/topic/10877/Notched-Music, Jul. 11, 2017—date downloaded, (11 pages).

Hidehiko Okamoto, et al., "Listening to tailor-made notched music reduces tinnitus loudness and tinnitus-related auditory cortex activity", (4 pages), PNAS, Jan. 19, 2010, vol. 107, No. 3, 1207-1210.

Von Gisela Schutte, "Spezial-CD soll Tinnitus-Patienten helfen", Die Welt, Jan. 17, 2000, (2 pages).

Jerad Hill, "iTinnitus Solutions 1.1 for iPhone Offers Sound Therapy for Tinnitus", "The Daily App Show", Feb. 19, 2014—date downloaded, pp. 1-2, XP055103023, (2 pages).

Alfonso Fernandez-Vazquez et al., "Design of IIR Notch Filters with Mazimally Flat or Equiripple Magnitude Characteristics", 14th EUSIPCO 2006, Florence, Italy, Sep. 4-8, 2006, 4 pages.

Dvdyke, "Frequency notch filtering possible?", Winamp & Shoutcast Forums, Mar. 12, 2010, 1 page.

Tinnitus Support Message Board, "Notched Music Therapy for Tinnitus—A Do it Your Self Video Guide to Tailor Made Therapy", Mar. 10, 2010, 65 pages.

Wikipedia, "Chebyshev filter", Downloaded from the Internet on Jun. 23, 2023, 9 pages.

Wikipedia, "Infinite impulse response", Downloaded from the Internet on Jun. 23, 2023, 7 pages.

Wilson et al., "Listening to Filtered Music as a Treatment Option for Tinnitus: A Review", 2010, 5 pages.

Winamp, "Media Player Help: Player Overview", 2010, 4 pages.

Winamp, "Plug-In Equalizer v1.6", downloaded from the Internet on Jul. 29, 2022, 2 pages.

DEVICE FOR PROVIDING AN AUDIO SIGNAL

CLAIM FOR PRIORITY

The present application is a national stage filing under 35 U.S.C 371 of PCT application number PCT/EP2019/086814, having an international filing date of Dec. 20, 2019, which claims priority to Switzerland patent application number 01600/18 having a filing date of Dec. 21, 2018, the disclosures of which are hereby incorporated by reference in their entireties.

TECHNICAL FIELD

The invention relates to a device for providing an audio signal for suppressing or decreasing a n user's tinnitus, and to a method for generating such audio signal or obtaining it by modifying a received audio signal.

BACKGROUND ART

Tinnitus is a perception of sound by a person when no external sound is present. It may have different frequency characteristics, such as a ringing, a clicking, a hiss or a roaring, and it may be perceived in one or both ears, or in the person in general. Tinnitus is a widespread symptom affecting more than 10% of people. Mostly it relates to subjective tinnitus which, in contrast to objective tinnitus, cannot be detected by people other than the person affected, but is a subjective perception of this person. Tinnitus may be caused by hearing loss, in particular a noise-induced hearing loss, e.g. through cochlear damage. However, tinnitus has also been associated with various neurologic, metabolic or psychiatric disorders.

There is currently no known cure for tinnitus. Despite increased research focused on tinnitus and various propositions for related therapies, tinnitus is still not fully understood and therapies mostly relate to fighting symptoms rather than cause. Such therapies include cognitive behavioral therapy, medication, hyperbaric oxygen therapy, acupuncture and various sound therapies. Sound therapies include applying hearing aids, or masking the tinnitus by means of a masker, i.e. drowning the perceived sound of tinnitus in other sounds, such that the person's attention is drawn to the other sounds in order to achieve a habituation. In another therapy, a noiser creates noise, e.g. broad-band noise, which again shall distract the person and lead to a habituation to the tinnitus. Maskers or noisers are also used in tinnitus retraining therapy (TRT) in addition to counselling of the person. Instead of a narrow-band masker or a broad-band noiser, further sounds may be used in tinnitus therapy, such as music, common environmental sounds, speech, sound of rushing water, etc. In addition, the sounds may be filtered as e.g. in notched music therapy, wherein a frequency range around the tinnitus is filtered out. Another approach is Coordinated Reset (CR) Neuromodulation, in particular by Adaptive Neuromodulation (ANM): Acoustic tones are delivered with different frequencies centered around a characteristic frequency of the person's tinnitus. Neuromodulation aims at reducing pathologically enhanced neural synchrony within primary auditory cortices, and hence decreasing the tinnitus perception.

A common feature of the described sound therapies is the massive amount of time that the affected person needs to be exposed to the sound to achieve any significant effect in decreasing the tinnitus, if at all, or at least in enhancing a quality of living with the so tinnitus. Such amount of time is typically in the range of several hours per day over a period of at least a year. It follows that such therapies severely interfere with the person's every-day life. Hence it is an object of the present invention to provide a device and a method for effectively decreasing or suppressing a user's tinnitus.

DISCLOSURE OF THE INVENTION

The general object to provide a device for effectively decreasing or suppressing a user's tinnitus is solved by the device according to claim 1.

According to a first aspect of the invention, the device for providing an audio signal for suppressing or decreasing a user's tinnitus comprises an identification unit for supporting a determination of at least one m parameter regarding the user's tinnitus; an adaptation unit configured to modify a received audio signal according to the at least one parameter, thereby obtaining the audio signal, or to generate the audio signal according to the at least one parameter; and an audio output unit configured to play the audio signal to the user. A defined frequency spectrum, also referred to as frequency characteristic or frequency range, that is applied in/to the audio signal is dependent on a tinnitus suppression frequency.

The tinnitus suppression frequency is defined as the frequency for which tinnitus suppression or deletion occurs. This means that a sound played to the user, which sound is at the tinnitus suppression frequency or obeys to the defined frequency spectrum as detailed later, will lead to a suppression or deletion of the user's tinnitus for a time duration called the interval of tinnitus suppression. It has been found that the tinnitus suppression frequency in many users coincides with the tinnitus frequency within a tolerance of +/−10%, i.e. a dominant frequency perceived by the user in the tinnitus. Hence the tinnitus frequency may be used as a proxy for the tinnitus suppression frequency. Thus, the tinnitus suppression frequency advantageously is the tinnitus frequency throughout the following description.

In an advantageous embodiment, the audio signal has a defined frequency spectrum comprising a peak of intensity with a peak frequency being one or more of: at the tinnitus suppression frequency, within a frequency range between one fourth of an octave below and one fourth of an octave above the tinnitus suppression frequency, at a frequency one or more octaves below and/or above the tinnitus suppression frequency, and within a frequency range between one fourth of an octave below and one fourth of an octave above the frequency one or more octaves below and/or above the tinnitus suppression frequency.

It has been observed with several test users, and it is an insight of the inventor, that playing an audio signal with such frequency spectrum to a user, who perceives a subjective tinnitus, decreases or suppresses the tinnitus. "Decreasing" shall mean that a loudness of the tinnitus is reduced, but still above a hearing threshold of the user, i.e. the tinnitus is still perceived but less loud. "Suppressing" shall mean that the loudness of the tinnitus is reduced to zero or at least below the hearing threshold of the user, i.e. the tinnitus is no longer perceived. After playing a finite audio signal with the described frequency spectrum, the tinnitus is decreased or suppressed for an interval of tinnitus suppression, also called a tinnitus deletion time, e.g. 5 s, 10 s, 30 s, 60 s, 2 min, 3 min, 10 min, an hour or even several hours for different users. Only after the interval of tinnitus deletion, the tinnitus recovers, and its loudness increases beyond the hearing threshold of the user until finally reaching again its original loudness. A huge advantage of using the device and playing the audio signal with the defined frequency spectrum to the user is that such treatment is simple, does not require much effort, and achieves the effect of suppressing the tinnitus very fast, i.e. on a time-scale of minutes—compared to months in other therapy forms of therapy as discussed in the background section. Still on the longterm, such use of the device may help to re-train neurons associated with tinnitus in the user's brain, and dismantle them on an organic level, such that the cause of tinnitus is remedied.

Further it has been observed that an exact form of the frequency spectrum of the audio signal is irrelevant to the effect of decreasing or suppressing the tinnitus as long as the above criteria for the peak frequency are met. This means that a sinus sound having intensity in only one frequency does the job, but also a narrow-band signal within half of an octave around the tinnitus suppression frequency. Such narrow-band signal preferably has a bandwidth equal to or less than half of an octave, or preferably equal to or less than a quarter of an octave, or preferably equal to or less than an eighth of an octave, or preferably equal to or less than 100 Hz. Preferably, the narrow-band signal has a bandwidth less than half of the bandwidth around the tinnitus suppression frequency provided for the locating the narrow-band signal, and preferably less than a quarter of such bandwidth, and preferably less than an eighth of such bandwidth. Also an audio signal having a peak frequency which is shifted one or more octaves compared to the tinnitus suppression frequency decreases or suppresses the tinnitus for some users. A narrow-band signal within half of an octave around the frequency shifted by the one or more octaves compared to the tinnitus suppression frequency may serve the purpose, too. The narrow-band signal preferably has a bandwidth equal to or less than half, or equal to or less than a quarter, or equal to or less than an eighth of an octave, or preferably equal to or less than 100 Hz within the given interval. Preferably, the narrow-band signal has a bandwidth less than half of the bandwidth around the frequency shifted by one or more octaves compared to the tinnitus suppression frequency, and preferably less than a quarter of such bandwidth, and preferably less than an eighth of such bandwidth. Even an audio signal with significant intensity in other frequencies has been observed to have the tinnitus decreasing or suppressing effect, provided that the frequency spectrum of the audio signal fulfills the above criteria. Thus the audio signal may be any sound, such as e.g. music, speech or environmental noise, whose frequency spectrum has been adapted to the defined frequency spectrum, e.g. by filtering.

Following from the above observation of the interval of tinnitus suppression, audio signals for tinnitus suppression preferably comprise signals that are continuous but may also comprise signals that are intermittent or alternating with time. "Intermittent" or "alternating" shall mean that any property of the audio signal is switched on and off, or changed repeatedly with time, such as a loudness or a frequency spectrum of the audio signal. An effective time of tinnitus suppression, i.e. the duration for which the user does not perceive the tinnitus, is theoretically infinite, if an interval of intermittency or alternation is shorter than or equal to the interval of tinnitus suppression.

Another advantage of the above-described device is the ease of use. Since the device comprises an identification unit, an adaptation unit as well as an audio output unit, it may be regarded as an all-in-one solution for providing an audio signal for suppressing or decreasing a user's tinnitus. Firstly the user is supported by the identification unit in determining at least one parameter regarding his/her tinnitus. Examples for the at least one parameter are:

- the tinnitus suppression frequency, i.e. a dominant frequency or a range of frequencies of the tinnitus sound; in this case, the adaptation unit is advantageously configured to modify a received audio signal such that it follows the defined frequency spectrum, thereby obtaining the audio signal, or to generate the audio signal such that it follows the frequency spectrum defined dependent on the tinnitus suppression frequency as described above;
- a perceived loudness of the tinnitus, i.e. a subjective measure on a scale from quiet to load which may e.g. be measured in sones;
- a hearing threshold of the user, also known as auditory threshold which may be frequency dependent;
- the interval of tinnitus suppression, i.e. the duration of silence or non-perceivable tinnitus after one-time playing the audio signal with the defined frequency spectrum;
- a minimum necessary loudness of the audio signal in order to achieve tinnitus suppression;
- a minimum necessary duration of the audio signal in order to achieve tinnitus suppression.

Secondly the audio signal is generated, e.g. synthetically from a sound sample, or modified from the received audio signal according to the at least one parameter. This second step is preferably done automatically after the first step on the basis of the at least one parameter determined in the first step. Or in other words, modifying or generating the audio signal does not require any further user inputs, such as further parameter values, or any further user selections, such as a track selection. Hence, an adaptation unit is provided and is configured to automatically convert the at least one determined user specific parameter relating to the user's tinnitus into a parameter of the audio signal. Accordingly, the determined one or more parameters are reflected in the audio signal which is performed by the adaptation unit. Preferably, a or each determined parameter is converted in one of a frequency parameter of the audio signal, an amplitude parameter of the audio signal, or a timing parameter in the audio signal. In one example, a basic appearance of the audio signal is predefined: E.g. a time characteristic of the audio signal is predefined in that it shall be an intermittent audio signal. E.g., in addition, the frequency characteristic of the audio signal shall be predefined in that only the user specific tinnitus suppression frequency shall be used in form of a sinus signal. E.g. in addition, an amplitude characteristic of the audio signal shall be predefined in that only peaks of a minimum required loudness for suppressing or decreasing the user's tinnitus or below the users hearing threshold shall be used. Hence, in this example, the user specific user tinnitus suppression frequency is determined first by support of the device. In a next step, pulses of such tinnitus suppression frequency are played to the user at varying loudness by means of the device in order to identify the minimum required loudness of the audio signal for suppressing or decreasing the user's tinnitus. In another step, pulses at or above the minimum required loudness of the audio signal for suppressing or decreasing the user's tinnitus are played to the user at varying intervals in order to determine the interval of tinnitus suppression. Having measured these parameters, the basic appearance/general layout provided for the audio signal is adjusted, i.e. parameters of the audio signal are automatically set based on the measured user specific parameters. I.e. the frequency of the peaks in the audio signal is set to the tinnitus suppression frequency, the intervals between the peaks in the audio signal are set to or less than the determined user specific interval of tinnitus suppression. And the amplitude of the peaks are set to or at most+10% of the determined minimum required loudness of the audio signal for suppressing or decreasing the user's tinnitus.

Hence, in one embodiment, an audio signal predefined in its characteristics, and preferably predefined in its frequency characteristic, its timing characteristic, and its amplitude characteristic, is finalized in its parameters by means of the one or more determined user specific tinnitus related parameters. However, in any case, the audio signal has a frequency characteristic which is dependent on the user specific tinnitus suppression frequency.

In each determination of a tinnitus parameter, the device may use an iterative approach in sequentially offering sounds with a varying parameter to the user and requesting for feedback. E.g., in the determination of the required loudness for the audio signal, be it of peaks of an intermittent signal or the loudness of a continuous signal, test sounds with varying loudness may n be played to the user for identifying the loudness at which a tinnitus suppression just can be achieved.

In a preferred embodiment, the adaptation unit is configured to modify the received audio signal according to the defined frequency spectrum and based on the at least one parameter, or is configured to modify the received audio signal according to the defined frequency spectrum based on the at least one parameter. Or the adaptation unit is configured to generate the audio signal according to the defined frequency spectrum and based on the at least one parameter, or is configured to generate the audio signal according to the defined frequency spectrum based on the at least one parameter.

In has been found that the at least one parameter may vary over time for the user. Hence the identification may support a re-determination of the at least one parameter regarding the user's tinnitus, e.g. within a regular time interval or when the user feels that the value of the at least one parameter does not fit his/her perception any longer. Such re-determined at least one parameter will then again be used as new basis for the modification or generation of the audio signal.

It is evident that such device is not only easy to use for the user, but that it also makes the audio signal played to the user better adapted to his/her current situation. Both factors typically lead to a better appreciation of the device by the user, hence a longer use and likely a greater success in decreasing or suppressing the user's tinnitus.

From the above discussion, it is clear that the audio signal for suppressing or decreasing a user's tinnitus as well as the device for providing the audio signal may take various forms. Numerous combinations of the different features are possible to achieve the tinnitus decreasing or suppressing effect. All these combinations of the different features are understood to be comprised in the following disclosure of embodiments.

Preferably, the identification unit is configured to support a determination of the tinnitus suppression frequency. The identification unit is advantageously configured to play sounds of different frequencies to the user, to prompt an input of the user in response to the sounds of different frequencies, and to determine the tinnitus suppression frequency by evaluating the input. The determination may be done by presenting a sequence of sounds with continuously or stepwise rising or falling frequency to the user, and letting the user identify the frequency which suppresses or deletes the tinnitus, in particular which suppresses or deletes the tinnitus most effectively, e.g. to the lowest tinnitus loudness or for the longest interval of tinnitus suppression.

Alternatively, the tinnitus frequency may be taken as a proxy for the tinnitus suppression frequency as described above. In that case, the determination may be done by presenting a sequence of sounds with continuously rising or falling frequency to the user, and letting the user identify the frequency closest to the perceived tinnitus. Alternatively, the determination may be achieved by letting the user compare the tinnitus with one or two sounds of certain frequencies, and adapting the certain frequencies to the user's response.

Preferably, the identification unit is configured to support a determination of the perceived loudness of the tinnitus by playing sounds of different loudness to the user, prompting an input of the user in response to the sounds, and by determining the perceived loudness of the tinnitus by evaluating the input. This may be achieved in an analogous manner as the determination of the tinnitus frequency above.

In an embodiment, the at least one parameter comprises a minimum required loudness of the audio signal for suppressing or decreasing the user's tinnitus. The identification unit is configured to support a determination of the minimum required loudness. This may be done in the following way: The identification unit is configured to play sounds of different loudness to the user, to prompt an input of the user dependent on the tinnitus being suppressed or decreased, and to determine the minimum required loudness by evaluating the input. Advantageously the audio signal then played to the user has a loudness equal to the minimum required loudness within a tolerance of 10%. Such tolerance in particular relates to a value of the loudness measured or expressed in dB. Thus the user is not disturbed by the audio signal more than necessary.

Advantageously the identification unit is configured to support a regular re-determination of the minimum required loudness, in particular every week or month. Thus the value of the minimum required loudness may be adapted to changed conditions and perceptions of the user over time. In particular, the adaptation unit is then configured to adapt the audio signal to the re-determined minimum required loudness.

Additionally of alternatively, the adaptation unit may be configured to gradually lower the loudness of the audio signal over time starting from the minimum required loudness. Such gradual lowering of the loudness takes into account an empirical evolution of the minimum required loudness observed in users, which shows a decrease in minimum required loudness over time. However, at some point, the loudness of the played audio signal may be lower than the minimum required loudness for achieving tinnitus suppression in the user. For that case, the identification unit is advantageously configured to accept a user input regarding a re-appearance of the tinnitus. In general, the adaptation unit may be configured to increase or decrease the loudness of the audio signal by a defined amount, which in particular is in a range between 1 and 5 dB, e.g. 2 dB, in response to the user input.

Advantageously, the identification unit is configured to support a determination of the hearing threshold by playing sounds of different loudness to the user, prompting an input of the user in response to the sounds, and by determining the hearing threshold by evaluating the input. In particular the hearing threshold may be determined in dependence on the frequency, i.e. an audiogram of the user is determined.

In an embodiment, the identification unit is configured to support a determination of the interval of tinnitus suppression by playing a sound with the defined frequency spectrum to the user, prompting an input of the user in response to the sound, and by determining the interval of tinnitus suppression by evaluating the input. This may be achieved by prompting the user to press a button when he starts to perceive the tinnitus again after the sound has been played.

One or more of parameters as the determined tinnitus suppression frequency, tinnitus loudness, hearing threshold, and interval of tinnitus suppression are preferably used to adapt the audio signal played to the user. In this way, the audio signal may be optimally fitted to the user. In particular, the parameters may be determined by the user anew, and the audio signal may be adapted to the new parameters for an optimal effect of tinnitus suppression.

For this reason, the device comprises the adaptation unit configured to generate the audio signal according to the defined frequency range. In an embodiment, the adaptation unit generates a sinus signal on the tinnitus suppression frequency, or a narrow-band signal having the defined frequency spectrum with respect to the determined tinnitus suppression frequency. In another embodiment, the audio output unit generates the audio signal receiving a frequency characteristic that has been determined by the adaptation unit based on the tinnitus suppression frequency from the identification unit.

Alternatively, the adaptation unit may be configured to modify a frequency spectrum of a received audio signal according to the defined frequency range. The received audio signal may comprise any sound or noise, in particular one or more of music, speech, environmental sounds, e.g. recorded real-time in the surrounding of the user, white noise, pink noise, brown noise, and a tinnitus habituation sound. In this case, the adaptation unit may comprise a filter configured to amplify frequencies within the defined frequency spectrum, and/or to attenuate frequencies outside the defined frequency spectrum. The adaptation or attenuation of frequencies by the adaptation unit is preferably at least 25%, in particular more than 50%. For these purposes, the device may comprise a microphone configured to record the received audio signal, wherein the received audio signal is provided to the adaptation unit. Alternatively, the received audio signal may be provided to the adaptation unit from a database, in particular wherein the database is stored in a memory of the device.

The tinnitus habituation sound mentioned above is preferably adapted to draw a person's attention to itself and away from the tinnitus, i.e. the person may be distracted from the tinnitus, and a habituation to the tinnitus may be achieved. Hence it may be advantageous to combine the effects of such tinnitus habituation sound with the effect of playing an audio signal with the defined frequency spectrum according to the present invention in order to achieve an even better suppression of perceived tinnitus.

In an embodiment, the adaptation unit is configured to decrease the loudness of the audio signal over time continuously or stepwise. This means the user will hear continuous sounds, e.g. music, or intermittent sounds that become quieter over time, e.g. decreasing from 80 dB to 40 dB as a default. At some point in time, the acoustic energy within the audio signal, in particular in the defined frequency spectrum, will not suffice in order to decrease or suppress the tinnitus. At that time a user interaction may be useful. In particular the identification unit is configured to accept a user input, e.g. a press on a button, when the user input starts to perceive again the tinnitus. Further the identification unit may be configured to re-determine the at least one parameter, in particular the loudness of the audio signal, dependent on the user input. A reasonable choice is e.g. to set the loudness of the audio signal just above or e.g. 10 dB above its level when the user started to perceive the tinnitus again.

The idea of the previous embodiment may analogously be applied to other parameters, e.g. to the interval of tinnitus suppression or deletion. In such embodiment, the adaptation unit may be configured to increase the interval of sounds with the defined frequency spectrum over time continuously or stepwise, e.g. as a default from an interval of 5 s or 10 s up to 60 s or 10 min. In reaction to a user input when the user starts to perceive again the tinnitus, the identification unit is configured to re-determine the sound interval and to preferably set it just below the so re-determined interval of tinnitus suppression.

The defined frequency spectrum of the audio signal preferably comprises a narrow-bandwidth characteristic within half of an octave around the tinnitus suppression frequency and/or around the frequency one octave below the tinnitus suppression frequency. Good success of complete tinnitus suppression have been achieved by such audio signal. Alternatively, the defined frequency spectrum may comprise a narrow-bandwidth characteristic within one fourth, or even one eighth, of an octave around the tinnitus suppression frequency and/or around the frequency one octave below the tinnitus suppression frequency. Also such forms of the frequency spectrum suffice to achieve total tinnitus suppression in most users. The narrow-band signal preferably has a bandwidth equal to or less than half of an octave, or preferably equal to or less than a quarter of an octave, or preferably equal to or less than an eighth of an octave.

In an embodiment, the adaptation unit is further configured to split an acoustic energy in the defined frequency spectrum, e.g. defined by a pulse of defined length and amplitude as required to suppress the user's tinnitus, to different frequencies in the defined frequency spectrum, in particular to the frequency range around the frequency one or more octaves below or above the tinnitus suppression frequency. Such feature is particularly useful if the user suffers from hearing loss, i.e. his/her hearing threshold is higher than a normal hearing threshold, which may depend e.g. on frequency and age. Tinnitus is known to be often correlated with hearing loss in the sense that the tinnitus often occurs at or around the frequency of the largest hearing loss. Hence it is preferable that the adaptation unit is configured to perform the split of the acoustic energy dependent on the hearing threshold of the user. In an embodiment, the identification unit is configured to support a determination of the hearing threshold of the user, meaning that also the identification of the frequencies particularly affected by hearing loss is integrated in the device. Alternatively, the split of the acoustic energy may be performed according to a user's preferences, i.e. in order to generate a more agreeable user experience.

The defined frequency spectrum may correspond to a frequency spectrum of tinnitus, in particular of the user's tinnitus. This would lead to an optimal suppression of tinnitus. However, it has the disadvantage that the user has to listen to a tinnitus-like sound again, if it is played above the hearing threshold.

Alternatively, the audio signal may be a sinus signal, or be derived from a sinus signal. This comprises signals containing several frequency components in the defined frequency spectrum. In particular, the defined frequency spectrum may have zero intensity for frequencies other than the peak frequency, or outside the defined frequency spectrum.

Regarding the loudness of the audio signal, it is preferable that the loudness is below a perceived loudness of the tinnitus. In this way, the user is at least partly relieved from the pain of perceiving a sound at the tinnitus suppression frequency, in particular at the tinnitus frequency. More into that direction, the audio signal advantageously has a loudness equal to or below a hearing threshold of the user. Thus the user does neither perceive the audio signal on the tinnitus suppression frequency, in particular on the tinnitus frequency, nor the tinnitus itself.

In an embodiment, the audio signal is alternating or intermittent in time. In that case, the audio signal may alternate in loudness between a first loudness and a second loudness. In particular the first loudness is above the hearing threshold of the user, and/or the second loudness is equal to or below the hearing threshold of the user. A quality of a change-over between first loudness and second loudness has been observed to be irrelevant for the effect of tinnitus suppression. Hence the alternating or intermitting audio signal may comprise a steep slope between the first loudness and the second loudness. In particular a duration of the slope is preferably below 0.5 s or 0.1 s, and in particular the slope has the form of a step function. Such quality of change-over is well suited for short intermittent audio pulses. Alternatively, the alternating or intermittent audio signal may comprise a shallow slope between the first loudness and the second loudness, in particular wherein a duration of the slope is above 0.5 s or 1 s. Such longer change-over is particularly suitable for modifying an audio signal received from the environment or for adapting a piece of music.

In an embodiment, the interval of alternation or intermittency of the audio signal has a random duration. Preferably, however, the interval of alternation or intermittency of the audio signal is equal to or shorter than an interval of tinnitus suppression. Examples for the interval of alternation or intermittency are 10 s, 30 s or 60 s, in particular depending on the user's determined interval of tinnitus suppression. Thus the effective time of perceived tinnitus suppression for the user is theoretically infinite. In an advantageous embodiment, the interval of alternation or intermittency is synchronized with, i.e. equal to, the interval of tinnitus suppression, such that the user is not subjected to more audio pulses than necessary.

In an embodiment, the audio output unit is configured to play the audio signal to an ipsilateral ear in relation to the tinnitus, i.e. the same ear on which the user perceives the tinnitus, in particular exclusively to the ipsilateral ear. However, it may also be feasible to play the audio signal to a contralateral ear in relation to the tinnitus, in particular exclusively to the contralateral ear. All variants may show the desired effect of tinnitus suppression, but they are accepted more or less well depending on the user.

The audio output unit may further be configured to play a second audio signal with a second frequency spectrum to the user simultaneously with the sound, wherein the second frequency spectrum comprises a broader frequency range than the defined frequency spectrum. The second audio signal may comprise one or more of music, speech and environmental sounds. This means that the user may listen to such second audio signal, e.g. with a regular frequency spectrum, simultaneously which makes the use of the device more agreeable. Preferably, a loudness of the second audio signal is below the loudness of the audio signal. In the above case of an intermittent or alternating audio signal having a first and second loudness, the loudness of the second audio signal is preferably below the first loudness, and/or above the second loudness.

The second audio signal may alternatively or additionally comprise any sound, in particular one of a noise, e.g. white noise, pink noise, and brown noise, and a tinnitus habituation sound. As described above, a tinnitus habituation sound is preferably adapted to draw a person's attention to itself and away from the tinnitus, i.e. the person may be distracted from the tinnitus, and a habituation to the tinnitus may be achieved. Hence it may be advantageous to combine playing an audio signal with the defined frequency range with a tinnitus habituation sound played simultaneously in order to achieve an even better suppression of perceived tinnitus. Again, the audio signal may be played continuously or alternating.

Different embodiments of the device and the audio output unit are foreseen. In one embodiment, the audio output unit comprises a speaker or headphone configured to generate acoustic waves corresponding to the audio signal. Alternatively, the audio output unit may comprise an implant configured to generate acoustic waves corresponding to the audio signal directly in the user's hearing. Or the audio output unit may comprise a neuronal n stimulator configured to generate a sensation of the audio signal in the user's brain. In the latter case actual acoustic waves may even not be necessary for suppressing the tinnitus.

The device may be a mobile device, such as an MP3 player, or a mobile phone. Such devices are part of the every-day life of the user, such that playing the audio signal may be integrated into the user's life in an agreeable way. Alternatively, the device may be a hearing aid. A user with hearing loss will have and use a hearing aid anyway. Hence it is beneficial, if playing the audio signal, or in particular modifying a received audio signal according to the defined frequency spectrum, is performed by the hearing aid without the need of owning or wearing any further devices. Preferably, the hearing aid is configured to play the audio signal in addition to its regular function of rectifying hearing loss. This means that playing the audio signal for decreasing or suppressing the tinnitus goes beyond the normal function of a hearing aid. Assume that the hearing aid levels all frequencies perceived by the user to 100% of a regular perception of frequencies according to a standard audiogram. Then "playing the audio signal in addition to its regular function" means that frequencies in the defined frequency range are amplified to above 100%, in particular to at least 125%, 150%, or 200%. In an embodiment, the adaptation unit may be configured to generate or modify the audio signal according to the defined frequency range on top of a regular processing of the received audio signal for rectifying hearing loss.

In an embodiment, the device is a hearing aid or any other device performing functions of a hearing aid, in particular comprising a microphone for recording sounds in surroundings of the user. The received audio signal, i.e. the audio signal that is modified based on the at least one parameter by the adaptation unit, advantageously corresponds to an amplification of sounds in the surroundings of the user, which are in particular recorded by the microphone. For such embodiment, it is further advantageous that the adaptation unit is configured to enrich the audio signal with acoustic energy in the defined frequency spectrum if an acoustic energy in the defined frequency spectrum in the received audio signal is below a threshold, in particular below the hearing threshold of the user. In this way, suppression of the tinnitus may be achieved even if the surrounding sounds do not contain acoustic energy in the defined frequency spectrum.

Further, it is advantageous that the adaptation unit is configured to limit an output loudness, i.e. a total output loudness including the audio signal, to a level below a threshold. The threshold in particular is a feedback threshold if the device is a hearing aid or an earphone comprising a microphone. In this way, a feedback loop, in particular wherein a sound played by the device is fed back into the microphone and amplified again, leading to an annoying beep sound is avoided.

Particularly in the case of a hearing aid, but also for a general device, it is beneficial to limit the loudness or the acoustic energy in the audio signal to a certain threshold in order not to hurt the user's ear. In such embodiment, the adaptation unit is further configured to limit a loudness of the audio signal, in particular to a non-hurtful level of loudness, i.e. 105 dB within a tolerance of +/−10%. Alternatively, the adaptation unit is configured to limit an acoustic energy in the defined frequency spectrum, in particular to the non-hurtful level of acoustic energy.

In another embodiment, limiting the loudness of the acoustic energy in the audio signal is performed in order to avoid undesired acoustic feedback. This may be necessary for hardware-reasons, e.g. in a hearing aid or similar devices such as a mobile phone or headphones which amplify surrounding sounds. If the loudness or the n acoustic energy is not limited, the audio signal played by the hearing aid may be picked up again by the in-built microphone and amplified again, which may lead to a large, disturbing and in particular hurtful signal.

In an embodiment, the loudness or acoustic energy of the audio signal is not only limited, i.e. decreased for certain frequencies, but also increased for other frequencies, in particular in response to the limiting. Here again, the split of acoustic energy to the frequency range around the frequency one or more octaves below or above the tinnitus suppression frequency as described before may be useful. This may be implemented in the following way: The adaptation unit is configured to split at least a part of the acoustic energy which is neglected due to the limiting to the frequency range around the frequency one or more octaves below or above the tinnitus suppression frequency. This is useful, in particular in the case of a hearing aid, because the desired effect of tinnitus suppression is still achieved while the hurtful consequences of too much acoustic energy in a n certain frequency range are avoided.

In particular in the case of the device being a hearing aid or comprising functions of a hearing aid, which may be limited to frequencies below e.g. 6000 to 7000 Hz, i.e. a hearing aid limit frequency, due to limitations of its hardware or software, the following embodiment may be useful: If the tinnitus suppression frequency exceeds the hearing aid limit frequency, the frequency characteristic of the audio signal is absent a contribution at the tinnitus suppression frequency but instead at frequencies of the defined frequency spectrum which are one or more octaves lower than the tinnitus suppression frequency, and hence, in particular at frequencies inside the range of frequencies supported by the hardware. If the tinnitus suppression frequency is below the capability of the hardware, the suppression sound is advantageously played at the tinnitus suppression frequency, or at one or several octaves above the tinnitus suppression frequency. Preferably, the device, i.e. the adaptation unit automatically compares an identified tinnitus suppression frequency with the limit frequency of the hearing aid e.g. stored in the device.

In a different embodiment, octave-shifting of the acoustic energy in the suppression sound is useful, in case a user may have normal hearing capabilities up to a limit frequency but hearing loss and tinnitus above the limit frequency. In this case, playing a sound at the tinnitus suppression frequency is ineffective in terms of tinnitus suppression. Rather, it is preferred in this case to apply peaks in the audio signal at one or more octaves lower than the tinnitus suppression frequency, i.e. below the limit frequency. In this way, tinnitus suppression or deletion can still be achieved, even under severe hearing loss. This feature is particularly useful since studies show that the frequencies of tinnitus, of an optimum tinnitus suppression sound and of hearing loss often overlap. In reverse, this also applies to hearing loss at lower frequencies, e.g. below 100 to 200 Hz. Preferably, the device, i.e. the adaptation unit automatically compares an identified tinnitus suppression frequency with the limit frequency either stored in the device of identified by way of measurement.

In one embodiment of the present invention, the device, and specifically the adaptation unit is configured to apply the filter characteristic used for tinnitus suppression out of environmental sound. In the event that there is no environmental sound detected by the device, an artificial audio signal according to the requirements may be switched on at least for such period in time. In a different embodiment, the artificial audio signal may permanently be applied in addition to the application of the filter characteristic to environmental sound. In this case it is preferred, to either limit, i.e. clip the acoustic energy in the subject frequencies in case of environmental sound of high loudness, or to split the acoustic energy to other desired frequencies in the characteristic, e.g. an octave above or below the tinnitus suppression frequency.

In an embodiment, the identification unit may support the determination of the following parameters regarding the user's tinnitus in different steps:
1. the tinnitus suppression frequency or the tinnitus frequency, respectively, as described above; typically these frequencies are stable over time in most users;
2. the interval of tinnitus suppression; this is in particular necessary in case of an intermittent audio signal being played to the user;
3. the minimum required loudness; the order of steps 2 and 3 may be changed; also, the parameters in 2 and 3 may be re-determined after some time, e.g. after a week or after a month, in order to adapt to a changed perception by the user;
4. optionally in case of an intermittent signal, the duration of a pulse of the audio signal: Such duration is chosen to be long enough in order to achieve tinnitus suppression, and may then be optimized not to be longer than necessary in order not to be obtrusive to the user.

The sounds played to the user for determining subsequent parameters 2 to 4 are advantageously adapted to the earlier determined parameters 1 to 3.

A second aspect of the current invention relates to a method for generating an audio signal or modifying a received audio signal to obtain the audio signal on an electronic device according to claim 46. The audio signal, again, preferably has a defined frequency spectrum comprising a peak of intensity with a peak frequency being one or more of: at a tinnitus suppression frequency, within a frequency range between one fourth of an octave below and one fourth of an octave above the tinnitus suppression frequency, at a frequency one or more octaves below or above the tinnitus suppression frequency, and within a frequency range between one fourth of an octave below and one fourth of an octave above the frequency one or more octaves below or above the tinnitus suppression frequency.

The method preferably comprises the steps of supporting a determination of at least one parameter regarding a user's tinnitus, modifying the received audio signal according to the at least one parameter, thereby obtaining the audio signal, or generating the audio signal according to the at least one parameter, and playing the audio signal to a user. In particular the method is performed on a device as discussed above, and the audio signal also preferably comprises the properties discussed above. Further the method advantageously comprises the step of identifying one or more of the user's tinnitus suppression frequency, tinnitus loudness, interval of tinnitus suppression, and hearing threshold, in particular by using the device as discussed above.

A further aspect of the current invention relates to a computer program comprising instructions which, when the program is executed by a processor of an electronic device, cause the electronic device to carry out the steps of the above method. Preferably, the computer program is stored on a computer-readable data carrier.

Preferably, a device for providing an audio signal for suppressing or decreasing a user's tinnitus comprises an audio output unit configured to play the audio signal to the user, wherein the audio signal has a is defined frequency spectrum comprising a peak of intensity with a peak frequency being one or more of: at a tinnitus suppression frequency; within a frequency range between one fourth of an octave below and one fourth of an octave above the tinnitus suppression frequency; at a frequency one or more octaves below or above the tinnitus suppression frequency; and within a frequency range between one fourth of an octave below and one fourth of an octave above the frequency one or more octaves below or above the tinnitus suppression frequency.

Preferably, the device further comprises an identification unit for supporting a determination of the tinnitus suppression frequency.

Preferably, the identification unit is configured to play sounds of different frequencies to the user, to prompt an input of the user in response to the sounds of different frequencies, and to determine the tinnitus suppression frequency by evaluating the input.

Preferably, the device further comprises an adaptation unit configured to generate the audio signal according to the defined frequency range.

Preferably, the device further comprises an adaptation unit configured to modify a frequency spectrum of a received audio signal according to the defined frequency range.

Preferably, the adaptation unit comprises a filter configured to amplify frequencies within the defined frequency spectrum, and/or to attenuate frequencies outside the defined frequency spectrum.

Preferably, an adaptation or attenuation of frequencies by the adaptation unit is at least 25%, in particular more than 50%.

Preferably, the defined frequency spectrum comprises a narrow-bandwidth characteristic within half of an octave around the tinnitus suppression frequency and/or around the frequency one octave below the tinnitus suppression frequency.

Preferably, the defined frequency spectrum comprises a narrow-bandwidth characteristic within one fourth of an octave around the tinnitus suppression frequency and/or around the frequency one octave below the tinnitus suppression frequency.

Preferably, the defined frequency spectrum comprises a narrow-bandwidth characteristic within one eighth of an octave around the tinnitus suppression frequency and/or around the frequency one octave below the tinnitus suppression frequency.

Preferably, the defined frequency spectrum corresponds to a frequency spectrum of tinnitus, in particular of the user's tinnitus.

Preferably, the audio signal is a sinus signal, or is derived from a sinus signal.

Preferably, the defined frequency spectrum has zero intensity for frequencies other than the peak frequency.

Preferably, the audio signal has a loudness below or above a perceived loudness of the tinnitus.

Preferably, the identification unit is further configured to support a determination of the perceived loudness of the tinnitus by playing sounds of different loudness to the user, prompting an input of the user in response to the sounds, and by determining the perceived loudness of the tinnitus by evaluating the input.

Preferably, the audio signal has a loudness equal to or below a hearing threshold of the user.

Preferably, the identification unit is further configured to support a determination of the hearing threshold by playing sounds of different loudness to the user, prompting an input of the user in response to the sounds, and by determining the hearing threshold by evaluating the input.

Preferably, the audio signal is continuous in time.

Preferably, the audio signal is alternating or intermittent in time.

Preferably, the audio signal alternates in loudness between a first loudness and a second loudness, in particular wherein the first loudness is above the hearing threshold of the user, and in particular wherein the second loudness is equal to or below the hearing threshold of the user.

Preferably, the alternating or intermitting audio signal comprises a steep slope between the first loudness and the second loudness, in particular wherein a duration of the slope is below 0.5 s or is below 0.1 s, in particular the slope has the form of a step function.

Preferably, the alternating or intermitting audio signal comprises a shallow slope between the first loudness and the second loudness, in particular wherein a duration of the slope is above 0.5 s or is below 1 s.

Preferably, an interval of alternation or intermittency of the audio signal has a random duration.

Preferably, an interval of alternation or intermittency of the audio signal is equal to or shorter than an interval of tinnitus suppression, in particular wherein the interval of alternation or intermittency is in the range of 5 s, 10 s, 20 s, 30 s, 60 s, 5 min, 10 min to 1 h.

Preferably, the identification unit is further configured to support a determination of the interval of tinnitus suppression by playing a sound with the defined frequency spectrum to the user, prompting an input of the user in response to the sound, and by determining the interval of tinnitus suppression by evaluating the input.

Preferably, the interval of alternation or intermittency is synchronized with the interval of tinnitus suppression.

Preferably, the device further comprises a microphone configured to record the received audio signal, wherein the received audio signal is provided to the adaptation unit.

Preferably, the adaptation unit is configured to receive the audio signal from a database, in particular wherein the database is stored in a memory of the device.

Preferably, the received audio signal comprises one or more of music, speech, environmental sounds, white noise, pink noise, brown noise, and a tinnitus habituation sound.

Preferably, the audio output unit is further configured to play the audio signal to an ipsilateral ear in relation to the tinnitus, in particular exclusively to the ipsilateral ear.

Preferably, the audio output unit is further configured to play the audio signal to a contralateral ear in relation to the tinnitus, in particular exclusively to the contralateral ear.

Preferably, the audio output unit is further configured to play a second audio signal with a second frequency spectrum to the user simultaneously with the sound, wherein the second frequency spectrum comprises a broader frequency range than the defined frequency spectrum.

Preferably, the second audio signal comprises one or more of music, speech, environmental sounds, white noise, pink noise, brown noise, and a tinnitus habituation sound.

Preferably, a loudness of the second audio signal is below the loudness of the audio signal.

Preferably, a loudness of the second audio signal is below the first loudness, in particular wherein the loudness of the second audio signal is above the second loudness.

Preferably, the audio output unit comprises a speaker or headphone configured to generate acoustic waves corresponding to the audio signal.

Preferably, the device is an MP3 or other digital audio files player.

Preferably, the device is a mobile phone.

Preferably, the device is an earphone, e.g. having functionality to manually or automatically adapt a frequency content of the played audio signal.

Preferably, the device is a hearing aid.

Preferably, the hearing aid is configured to play the audio signal in addition to its regular function of rectifying hearing loss.

Preferably, the adaptation unit is configured to generate or modify the audio signal according to the defined frequency range on top of a regular processing of the received audio signal for rectifying hearing loss.

Preferably, the audio output unit comprises an implant configured to generate acoustic waves corresponding to the audio signal directly in the user's hearing.

Preferably, the audio output unit comprises a neuronal stimulator configured to generate a sensation of the audio signal in the user's brain.

Preferably, in a method for generating an audio signal or modifying a received audio signal to obtain the audio signal on an electronic device, the audio signal has a defined frequency spectrum comprising a peak of intensity with a peak frequency being one or more of: at a tinnitus suppression frequency; within a frequency range between one fourth of an octave below and one fourth of an octave above the tinnitus suppression frequency; at a frequency one or more octaves below or above the tinnitus suppression frequency; and within a frequency range between one fourth of an octave below and one fourth of an octave above the frequency one or more octaves below or above the tinnitus suppression frequency.

Preferably, the method comprises the steps of automatically generating or obtaining the audio signal, and playing the audio signal to a user, in particular being performed on the device described above.

Preferably, the method further comprises the step of identifying one or more of the user's tinnitus suppression frequency, tinnitus loudness, minimum required loudness, interval of tinnitus suppression and hearing threshold, in particular by using the device described above.

Preferably, a computer program comprises instructions which, when the program is executed by a processor of an electronic device, cause the electronic device to carry out the steps of the method described above.

Preferably, a computer-readable data carrier has stored thereon the computer program.

The described embodiments similarly pertain to the device, the method, the computer program, and the computer-readable data carrier. Synergetic effects may arise from different combinations of the embodiments although they might not be described in detail.

BRIEF DESCRIPTION OF THE DRAWINGS

The embodiments defined above and further features and advantages of the present invention can also be derived from the examples of embodiments described hereinafter which are explained with reference to the attached drawings. In the drawings, the figures show.

MODES FOR CARRYING OUT THE INVENTION

Figure 1:
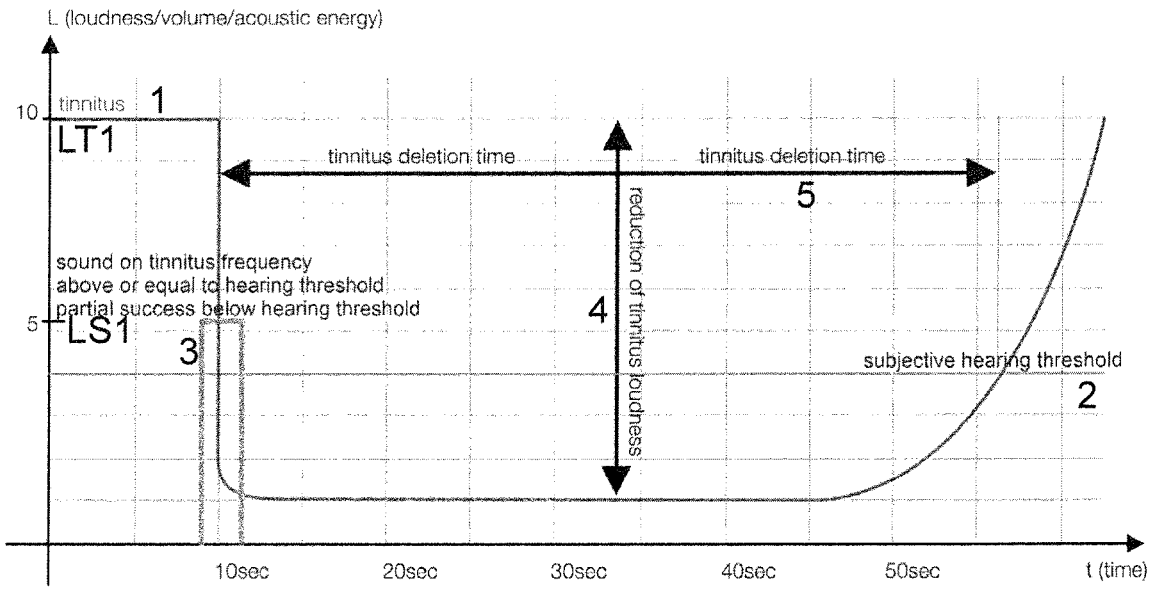
FIG. 1 a time diagram of an empiric finding of tinnitus deletion by a sound underlying a device and a method according to the following figures, FIGS. 2 and 3 time diagrams with continuous and intermittent sound, respectively, according to embodiments of the present invention, FIGS. 4 to 8 time diagrams of particular embodiments with continuous sound, FIGS. 9 to 14 time diagrams of particular embodiments with intermittent sound, FIGS. 15 to 18 time diagrams with boosted music or boosted sounds according to embodiments of the present invention, FIG. 19 a time diagram of different transition characteristics of a sound played according to embodiments of the present invention, FIGS. 20 to 24 time diagrams of an influence of an interval of sound intermittency or alternation on a degree of tinnitus suppression according to embodiments of the present invention, FIG. 25 a time diagram of an embodiment with continuous sound adapting to the minimum required loudness, FIGS. 26 to 28 time diagrams of embodiments with intermittent sounds adapted to the interval of tinnitus suppression, the minimum required loudness and the duration, respectively, FIGS. 29 to 31 frequency spectra of embodiments related to hardware limitations and hearing loss, respectively, FIG. 32a-c examples of frequency spectra of sounds applied according to embodiments of the present invention, FIG. 33 a schematic view of a mobile phone according to an embodiment of the present invention, FIGS. 34 to 37 block diagrams of various components of a device according to embodiments of the present invention, FIG. 38 a block diagram of an electronic device according to an embodiment of the present invention, FIG. 39 a system containing a medium for downloading software according to an embodiment of the present invention, FIG. 40 a flow chart of a method according to an embodiment of the present invention, and FIGS. 41a-c subroutines of the method as illustrated in FIG. 40.

Similar or relating components in the figures are provided with the same reference numerals. A "sound" may be understood as an audio signal or a sensation of such in general. "Playing a sound" to the user may be achieved in different ways, e.g. as usually by generating acoustic waves that are transmitted to the user's ear via air, or by creating the acoustic waves directly in the user's hearing via an implant, or by creating a sensation of the sound directly in the user's brain.

FIG. 1 shows a time diagram of an empiric finding of tinnitus deletion by a sound underlying a device and a method according to the subsequent figures. In FIG. 1 and in similar diagrams, the axis of abscissae indicates time t in arbitrary units or in seconds s, and the axis of ordinates indicates loudness L or an equivalent physical quantity such as volume or acoustic energy. A first line represents the course of a perception of the tinnitus 1 of a user over time. A second line shows a subjective hearing threshold 2 of the user. A third line indicates a sound 3 played to the user, i.e. the audio signal.

For times t<10 s, the user perceives the tinnitus 1 at a certain loudness LT1, which is above his/her hearing threshold 2. Both, the loudness LT1 of the tinnitus 1 and the hearing threshold 2 are specific for a user and may be measured, e.g. by comparison to different sounds of different loudness. The tinnitus 1 is further characterized by a frequency fT or a frequency range which gives it its characteristic sound, such as a ringing, a clicking, a hiss or a roaring. The hearing threshold of a user varies with frequency in general. In time diagrams such as FIG. 1, the subjective hearing threshold of a user at the frequency fT of tinnitus is indicated.

Around time t=10 s, a sound 3 is played to the user with loudness LS1, which is above the hearing threshold 2 as well. The sound 3 has a certain duration, e.g. 2 s, and a tinnitus suppression frequency equal or similar to the tinnitus frequency fT. "Similar" shall mean that a frequency spectrum of the sound 3 comprises a peak at the tinnitus suppression frequency or within a frequency range of half an octave or a fourth of an octave around the tinnitus suppression frequency. Moreover, "similar" shall mean that the frequency spectrum of the sound 3 may alternatively or additionally comprise a peak at an octave-shifted tinnitus suppression frequency obtained by shifting the tinnitus suppression frequency by one or more octaves; the peak in the frequency spectrum of the sound 3 may also fall into a frequency range of half an octave or a fourth of an octave around an octave-shifted tinnitus suppression frequency.

It is observed that correlated with playing the sound 3, the loudness of tinnitus 1 drops significantly by a reduction 4 of tinnitus loudness. In particular it drops below the hearing threshold 2, such that it is not perceived by the user any longer. Only in the time interval between t=46-60 s, the tinnitus 1 recovers to its original loudness LT1. In particular it starts to n be perceived by the user again, when the loudness curve of the tinnitus 1 crosses the hearing threshold 2 at around t=56 s in the example of FIG. 1. This means that the user has not perceived and not been bothered by the tinnitus 1 for a certain tinnitus deletion time 5, also called an interval of tinnitus suppression, which in the example of FIG. 1 has a duration of 46 s. The actual values of reduction 4 of tinnitus loudness and tinnitus deletion time 5 are different and characteristic for individual users. The tinnitus deletion time 5 has been observed to be in the range of 10 s, 30 s, 60 s or several minutes in test users. Such tinnitus deletion time 5 can be exploited in a device for suppressing tinnitus and a corresponding method, provided the reduction of tinnitus loudness is observed repeatedly when the playing of sound 3 is repeated. Such empirical finding is the basis of the devices for decreasing or suppressing the tinnitus and corresponding methods in the following figures.

Originally the empirical finding was made when users (number of test persons>10) reported difficulties in measuring their tinnitus frequency fT with reference sounds. The tinnitus stopped almost immediately, when they perceived a sound 3 or noise similar to their tinnitus frequency fT, wherein "similar" here and in the following shall have the above-defined meaning. The effect was observed to be repeatable. It was sufficient that the loudness LS1 of the sound was low, e.g. at or just above the hearing threshold 2, or even below. An example of a frequency spectrum Ft(f) of a sound 3 with only frequencies within a range fr around the tinnitus frequency fT present is given in FIG. 32a; such frequency spectrum is similar to the tinnitus frequency fT. It is explicitly noted that the effect of reduction 4 of tinnitus loudness is related to the sound 3 having the described frequency spectrum, which is defined in relation to the tinnitus frequency fT, not in relation to a hearing loss characteristic or similar. Sounds that evoked n the same effect include sinus sounds having intensity in only one or a few distinct frequencies, tinnitus-similar sounds, i.e. sounds having a frequency spectrum corresponding to the one of the perceived tinnitus, and even external sounds, such as music or speech, filtered such that they have a peak in their frequency spectrum around the tinnitus frequency fT.

More specifically, the above findings are true when the tinnitus frequency fT is replaced by the tinnitus suppression frequency. While the two frequencies coincide within a tolerance of +/−10% for most users, in general they may be different.

Moreover it was observed that the reduction 4 of tinnitus loudness also occurred when a sound 3 was played to the user that was different from the tinnitus suppression frequency, in particular the tinnitus frequency fT, by one or more octaves, i.e. an octave shift. An example of a sound 3 which is one octave lower than the tinnitus frequency fT is given in FIG. 32b; also such frequency spectrum is considered similar to the tinnitus frequency fT. In one test user, there was a very good success of tinnitus reduction 4 for the user at the tinnitus frequency fT=13 kHz; at a frequency of 6.5 kHz (fT minus one octave), there was still good success for this user; and at frequencies of 3.25 kHz and 1.6 kHz (fT minus two or three octaves), there was partial success. Further it was observed that the sound 3 may even have different characteristics, i.e. differing frequency spectrums, and nevertheless evoke the same effect of reduction 4 of tinnitus loudness, provided the sound 3 fulfills the criterion of being similar to the tinnitus suppression frequency. In particular the frequency spectrum of such sound 3 may comprise further frequencies outside the range of similarity to the tinnitus suppression frequency. The latter situation is depicted in FIG. 32c with a typical frequency spectrum Ft(f) of an external sound, such as music, that has low intensity for high frequencies, for which tinnitus occurs in most users. Therefore frequencies in the frequency range fr around the tinnitus suppression frequency are amplified, e.g. by a bandpass filter. The factor of amplification may typically be at least 25%, 50%, or more than 100%. The effect of tinnitus reduction 4 also occurred, when other external sounds were heard at the same time as the sound 3.

The effect observed with test users can be exploited to delete tinnitus in real time, i.e. immediately. On the other hand, the effect may also reduce tinnitus in the long term as synapses causing tinnitus may be deactivated repeatedly and over a sufficiently long period of time. Thus neurons or acquired synapses corresponding to the tinnitus are re-trained not to produce any additional activity which leads to the sensation of tinnitus. In this way, the tinnitus-causing synapses may be dismantled on a biological level due to lack of need or lack of use in a process inverse to an acquisition of tinnitus, and the cause of tinnitus is removed.

While FIG. 1 shows a sound 3 that has a lower loudness LS1 than the tinnitus, LS1<LT1, alternative embodiments may have LS1=LT1 or LS1>LT1. However, note that it may be difficult to determine an objective loudness of the tinnitus since tinnitus is a subjective phenomenon. For this purpose, it is assumed that the loudness of the tinnitus may be determined, e.g. by the user comparing the tinnitus to sounds of a known loudness and hence known acoustic energy.

In a recent study, it has been found that tinnitus suppression with an intermittent sound is particularly effective if the sound 3 in FIG. 1 is played with a loudness that is 10 dB above the initial loudness of the tinnitus 1, meaning LS1=LT1+10 dB. Note that this formula represents the median of an empirical study. The exact values vary between users. According to the study, a continuous sound is most effective in suppressing the tinnitus if it is played at the same or a similar loudness as the tinnitus, i.e. LS1=LT1 within a tolerance of +/−10%. Hence in general, it is preferred that the sound 3 is played with a loudness LS1 that is in the range between the tinnitus loudness LT1−10 dB and LT1+20 dB, in particular between LT1 and LT1+10 dB. A greater sound loudness LS1 would be disturbing and potentially harmful to the user.

Figure 2:
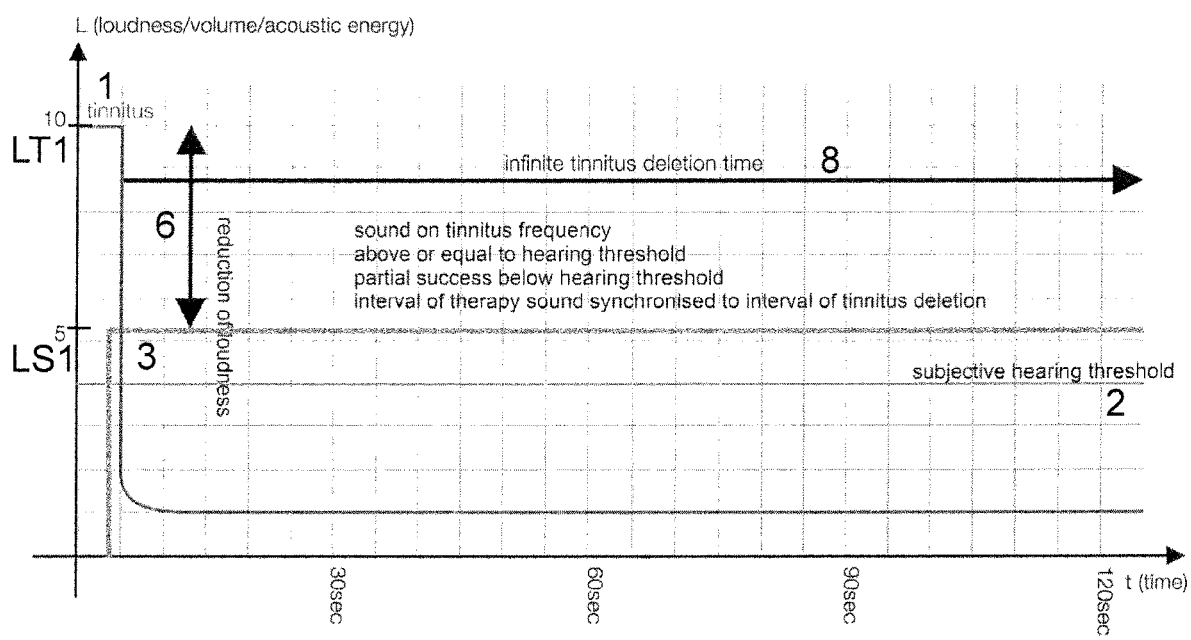

FIG. 2 shows a time diagram of a method with a continuous sound 3 according to an embodiment of the present invention. Also in this case, the tinnitus 1 drops by a reduction in loudness to below the subjective hearing threshold 2, when the sound 3 on or around the tinnitus suppression frequency sets in. Since the sound 3 is played continuously, the tinnitus deletion time 5 is infinite. The method with continuous sound 3 may advantageously be applied with pleasant sounds, such as music, speech or environmental sounds, filtered to boost frequencies similar to the tinnitus suppression frequency, e.g. by a bandpass filter. In FIG. 2, the sound 3 has a loudness LS1 above the hearing threshold 2. This means that there is a remaining loudness on the tinnitus suppression frequency due to the sound 3. The reduction 6 of loudness at the tinnitus suppression frequency is hence partial. However, success in reducing tinnitus loudness has partly also been achieved when LS1 is at or below the hearing threshold 2, see e.g. FIG. 6. In the latter case, the reduction 6 of loudness at the tinnitus suppression frequency is total. For that purpose, sinus sounds or colored noise is advantageously applied.

Figure 3:
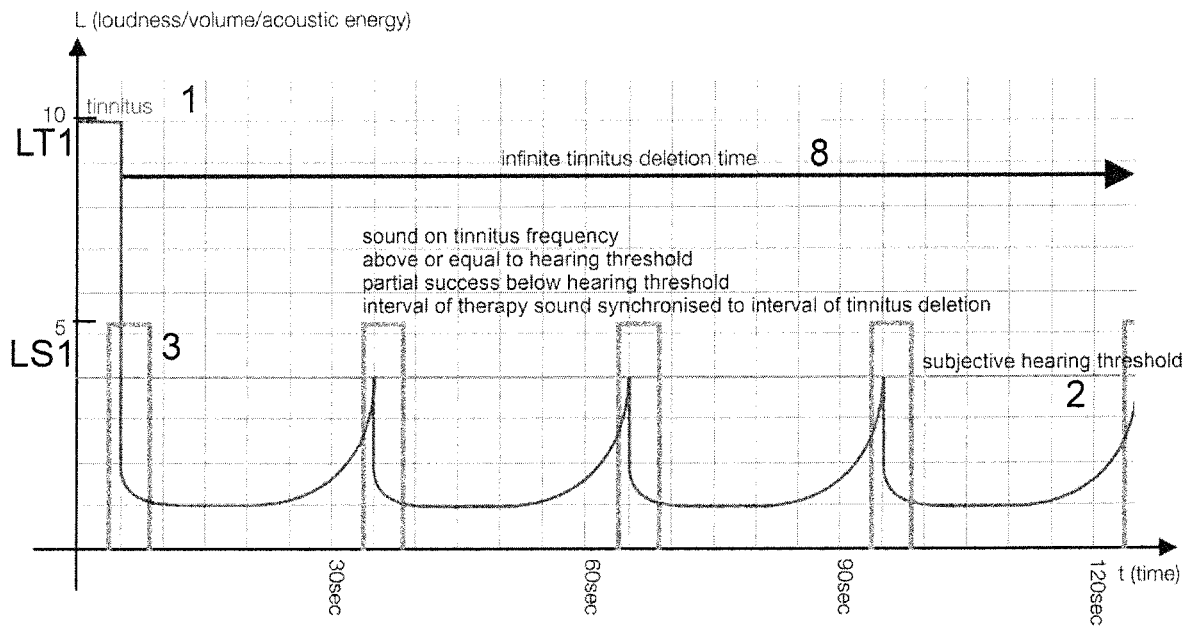

FIG. 3 shows a time diagram of a method with an intermittent sound 3 according to an embodiment of the present invention. The sound 3 again has a frequency spectrum similar to the tinnitus suppression frequency, but a duration of only 5 s, which suffices to cause the to tinnitus 1 to drop in loudness. In this case, the recovering tinnitus 1 reaches the hearing threshold 2 around 30 s after its deletion. Since the tinnitus deletion time 5 due to such an intermittent sound 3 may be known from measurements, the interval of sound intermittency is set n to the tinnitus deletion time 5, i.e. 30 s, such that the tinnitus is again suppressed when it becomes perceivable by the user. As a result, the effective tinnitus deletion time 8 may be extended, theoretically to infinity. Also the method with an intermittent sound 3 works with sounds of various frequency characteristics, e.g. sinus tones or noise, provided that their frequency spectrum is similar to the tinnitus suppression frequency. Partial success may again still be achieved when reducing the sound loudness LS1 below the hearing threshold 2.

A first step to be performed by an electronic device for suppressing tinnitus or in a corresponding method is preferably a measurement of the user's subjective tinnitus. The measurement may relate to one or more of a tinnitus suppression frequency, in particular the tinnitus frequency fT, i.e. the dominating frequency of tinnitus, a tinnitus suppression frequency spectrum, an interval of tinnitus suppression, a tinnitus loudness LT1, and a hearing threshold. The measurement may be performed by comparison with reference sounds, e.g. under the guidance of an audiologist or performed by the user himself/herself. Alternatively, the measurement may be a measurement of neuronal activity related to the user's hearing.

In a second step and as described above, a sound 3 with a frequency spectrum similar to the tinnitus suppression frequency is played to the user. Thus the tinnitus 1 is stopped or reduced or suppressed. The sound 3 may be of any narrow-bandwidth sound characteristic, meaning narrower than one third of an octave, including tinnitus-similar sounds and sinus-similar sounds. This n may be performed in quiet surroundings, or while other sounds are perceived at the same time. The sound 3 or a sensation of sound 3 may be achieved through a speaker, an earphone, customized hardware, a hearing aid, an implant or a device creating neuronal sensation of a sound.

Figure 4:
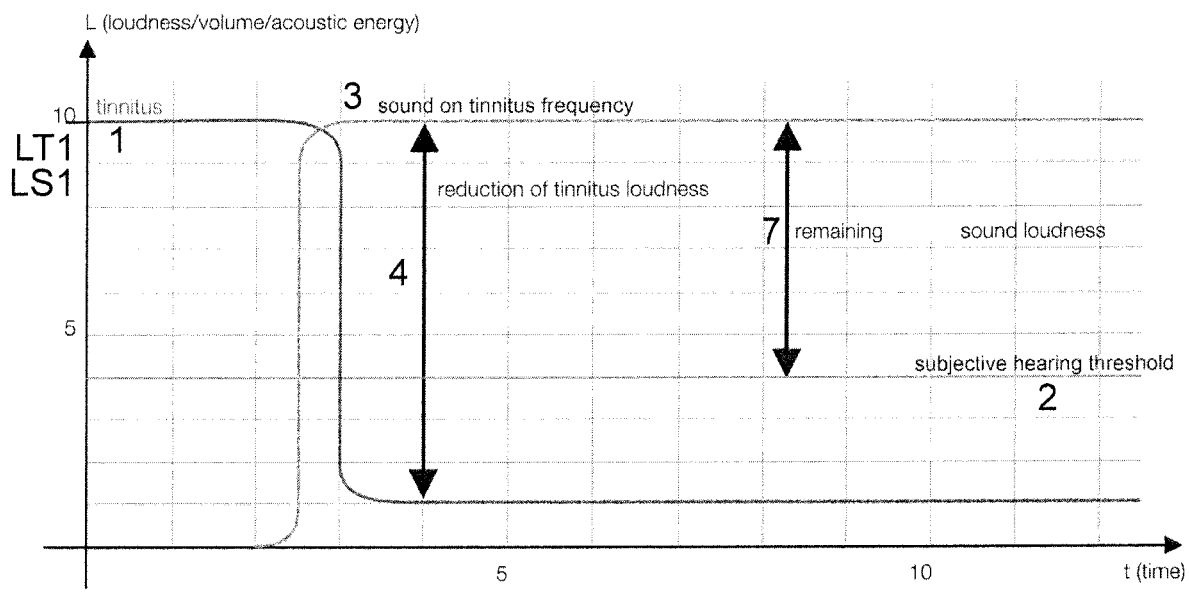

FIGS. 4 to 8 show time diagrams of particular embodiments of the second step with continuous sound building on the concept of FIG. 2. In FIG. 4, the loudness LS1 of the sound 3 is the same as the original tinnitus loudness LT1. The transition from zero loudness to loudness LS1 may be smooth, e.g. as shown, or abrupt, see also FIG. 19. Shortly after the sound 3 sets in, the tinnitus 1 is decreased by the reduction 4, and not perceived by the user any longer since its loudness is below the hearing threshold 2. However, now the user perceives the sound 3 similar to the tinnitus frequency fT with the same loudness LS1=LT1 as the tinnitus 1 before. As such there is no reduction in the remaining sound loudness 7 on the tinnitus frequency fT. But the sound 3 may be more pleasant and less agonizing than the tinnitus 1.

Figure 5:
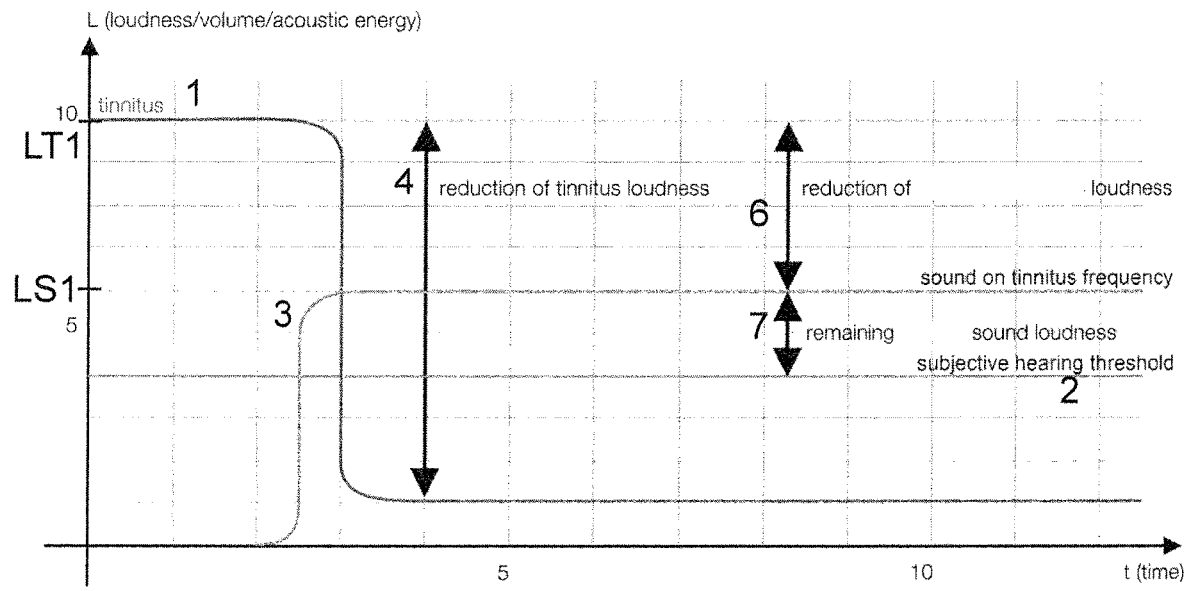

The time diagram of FIG. 5 differs from FIG. 4 in that the sound 3 has a lower loudness LS1 than the original tinnitus loudness LT1. The effect achieved through the sound 3 is again a reduction 4 of the tinnitus loudness below the hearing threshold 2. However, due to LS1<LT1 in this case, there is an effective reduction 6 of loudness on or around the tinnitus frequency fT. Thus a remaining loudness 7 on or around the tinnitus frequency fT is lower, such that the perceived sound is effectively decreased, and the user is at least partially relieved.

Figure 6:
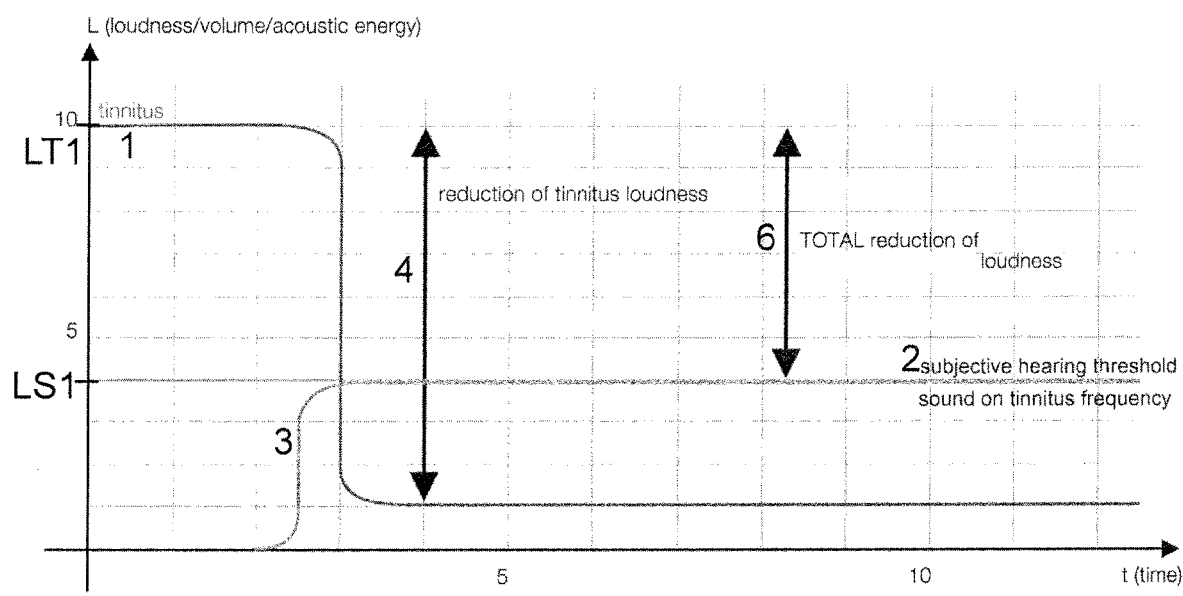

It has been found with several users that the method of FIGS. 4 and 5 also work when playing a sound 3 that is not consciously perceived by the user. It may be that conscious perception is not as relevant as subconscious perception by hypothalamus. This situation is shown in FIG. 6, wherein the loudness LS1 of the sound 3 is equal to or even below the hearing threshold 2 of the user around the tinnitus frequency fT. Again there is a reduction 4 of tinnitus 1. Since the user does not perceive the sound 3, he/she does not hear any remaining sound at the tinnitus frequency fT, such that the reduces 6 of loudness at the tinnitus frequency fT is total. Such situation is beneficial for a restructuring of the synapses causing the tinnitus because it completely breaks the feedback loop creating subjective tinnitus.

Figure 7:
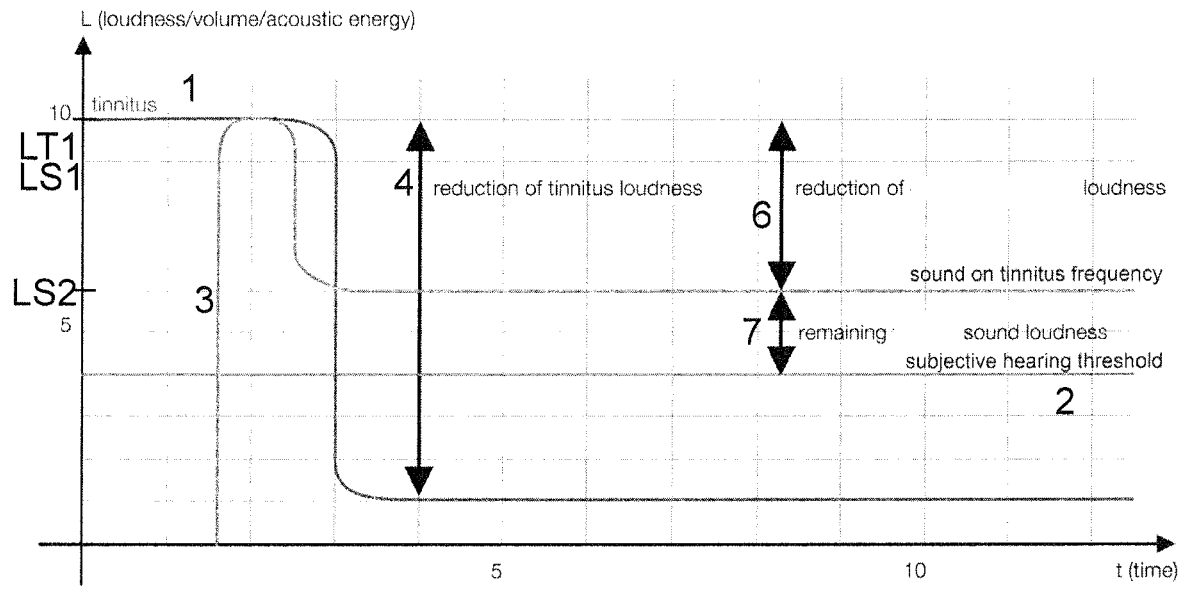
Figure 8:
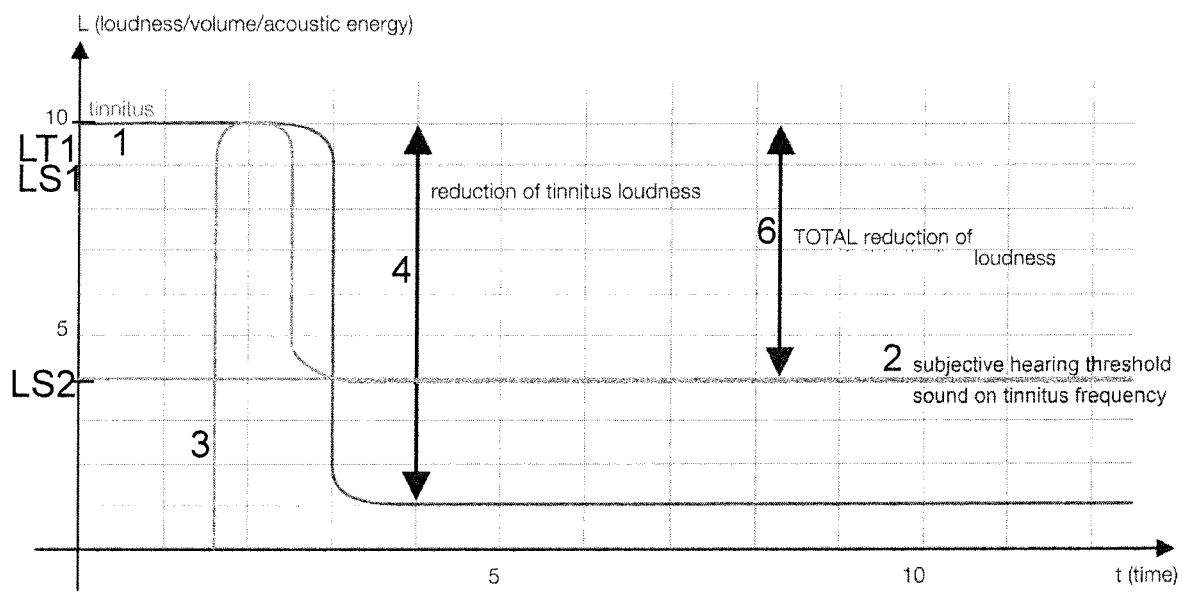

FIGS. 7 and 8 show advantageous modifications of the methods of FIGS. 5 and 6. When the sound 3 sets in, in the beginning it as a first loudness LS1, such as being equal to the tinnitus loudness LT1. Then the loudness of the sound 3 is reduced to a second loudness LS2, which is lower and played continuously. Such first sound impulse with a high loudness LS1 may improve the effect of tinnitus suppression in some users. Due to the different levels of the second loudness LS2 in FIGS. 7 and 8, the reduction 6 in loudness at the tinnitus frequency fT is partial in FIG. 7, and total in FIG. 8.

FIGS. 9 to 14 are time diagrams of particular embodiments of methods with intermittent sound. An intermittent sound 3 is played to the user, wherein the sound peaks have a loudness LS1, and in between the sound peaks there is zero loudness. The frequency spectrum of the sound 3 should be similar to the tinnitus suppression frequency, in particular the tinnitus frequency fT, as discussed above. The sound peaks have a duration of 1 s to 2 s, which is sufficient to yield a tinnitus suppression. Depending on and as required by the user, the sound peaks may also be longer. The time between peaks ideally corresponds to the user's tinnitus deletion time 5, e.g. 10 s, 30 s, or 60 s, but may also be shorter to achieve the same effect. Provided that the time between peaks is no longer than the tinnitus deletion time, the next peak of sound 3 sets in, when or before the tinnitus 1 has recovered to a loudness equal to the hearing threshold 2. In this way, a total cancellation of cumulative sound on the tinnitus suppression frequency is achieved during the time between the sound peaks, i.e. the time 8 of no perceivable tinnitus.

Figure 9:
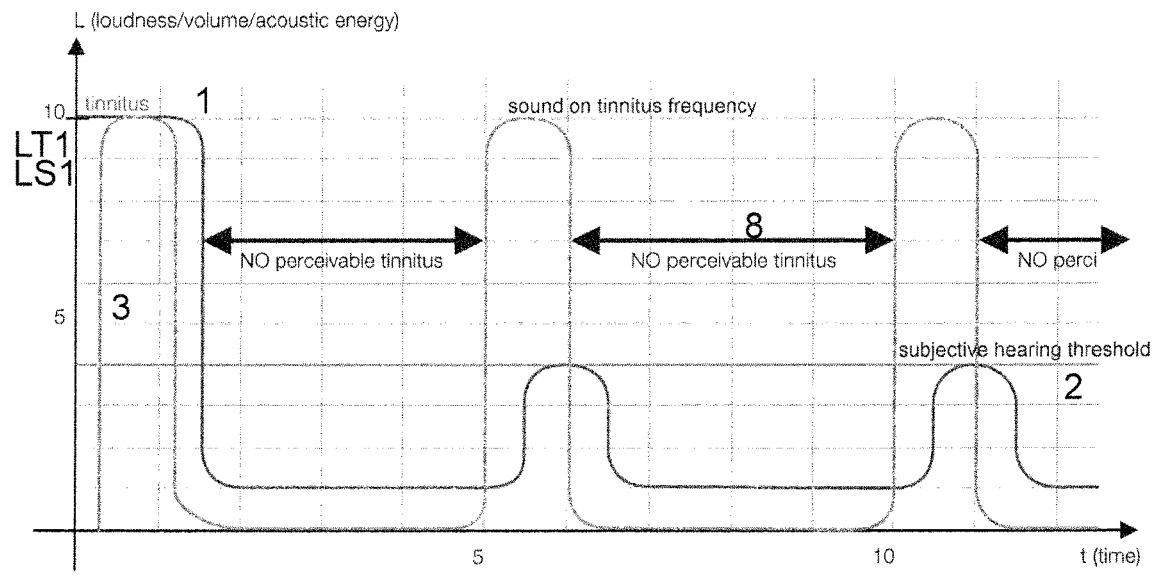

The intermittent sound 3 of FIG. 9 has a is loudness LS1 during peaks which is equal to the original tinnitus loudness LT1. All sound peaks have the same loudness LS1. This may e.g. be a beeping or intermittent noise with the required frequency spectrum.

Figure 10:
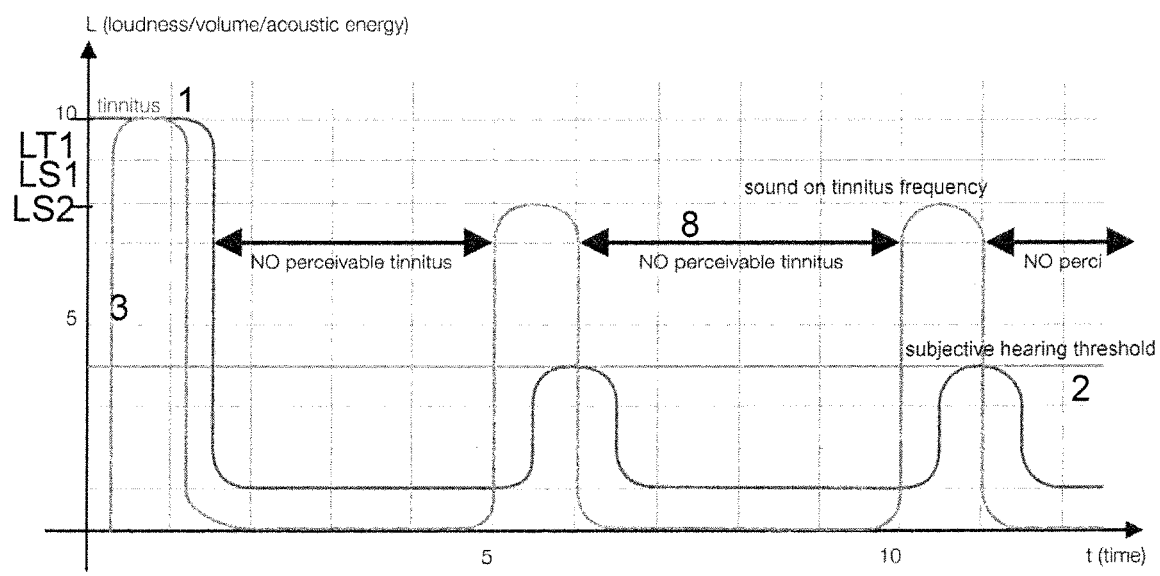
Figure 11:
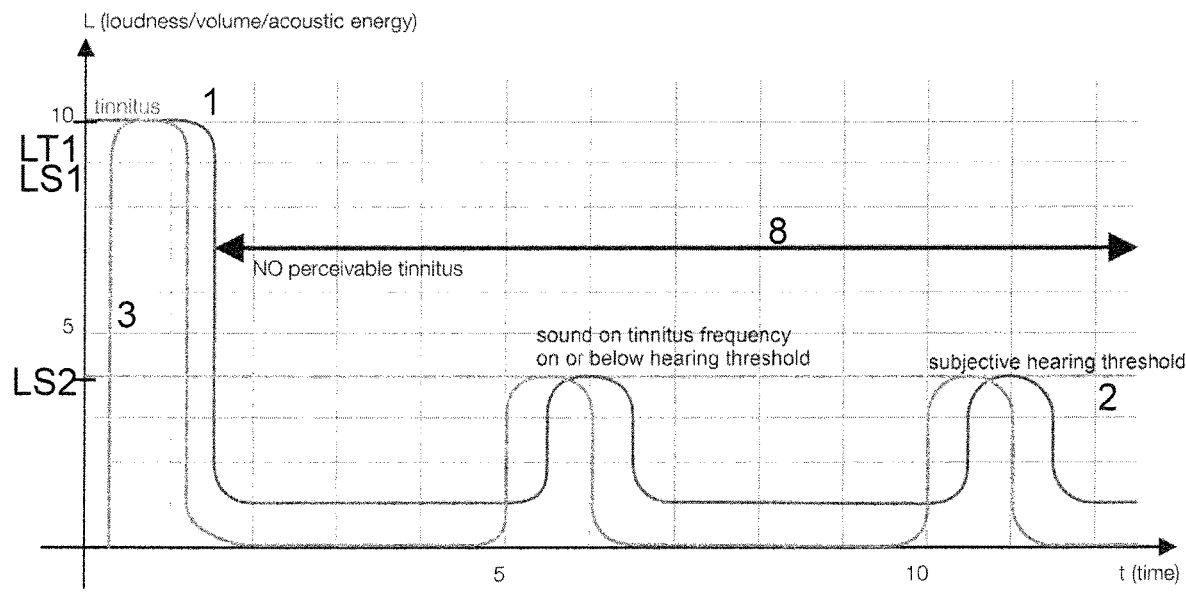

In FIG. 10, only the first peak of the intermittent sound 3 has a loudness LS1 equal to the original tinnitus loudness LT1. The first peak suppresses the original tinnitus. Subsequent peaks have a loudness LS2 which is lower than LS1, but above the hearing threshold 2. In FIG. 11, which shows a similar method, the subsequent peaks have a loudness LS2 which is equal to the hearing threshold 2. In both cases, the subsequent peaks are sufficient in order to suppress the recovering tinnitus anew. The method according to FIG. 11 has the advantage that after a first sound peak with loudness LS1, so which is consciously perceived by the user, the subsequent peaks with loudness LS2 are not consciously perceived by the user. Hence an every-day life of the user is not disturbed.

Figure 12:
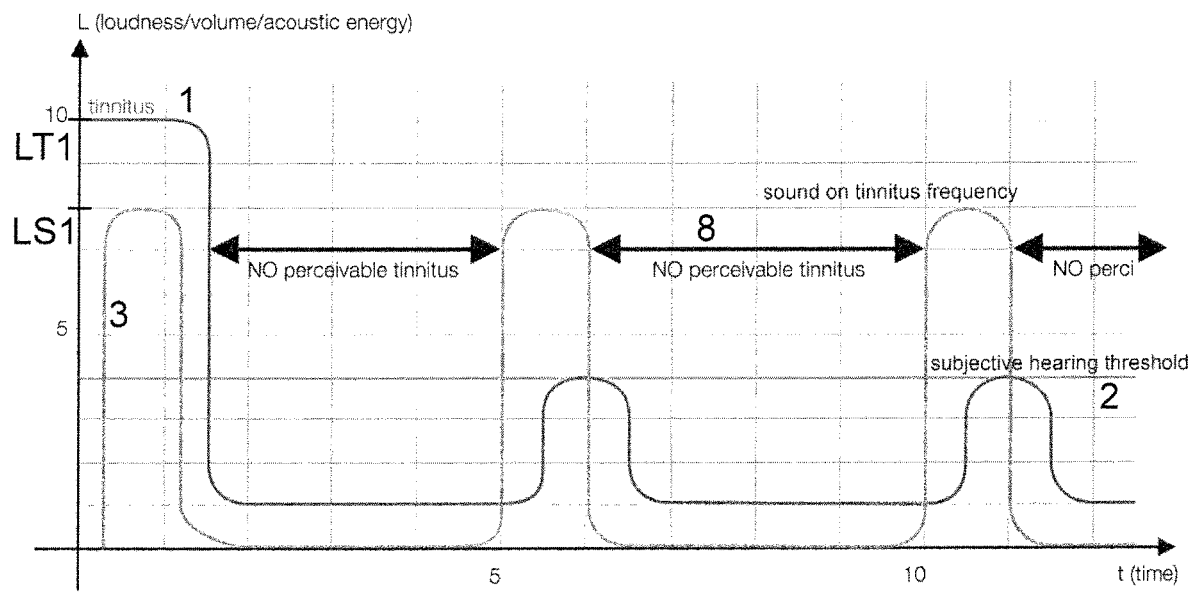
Figure 13:
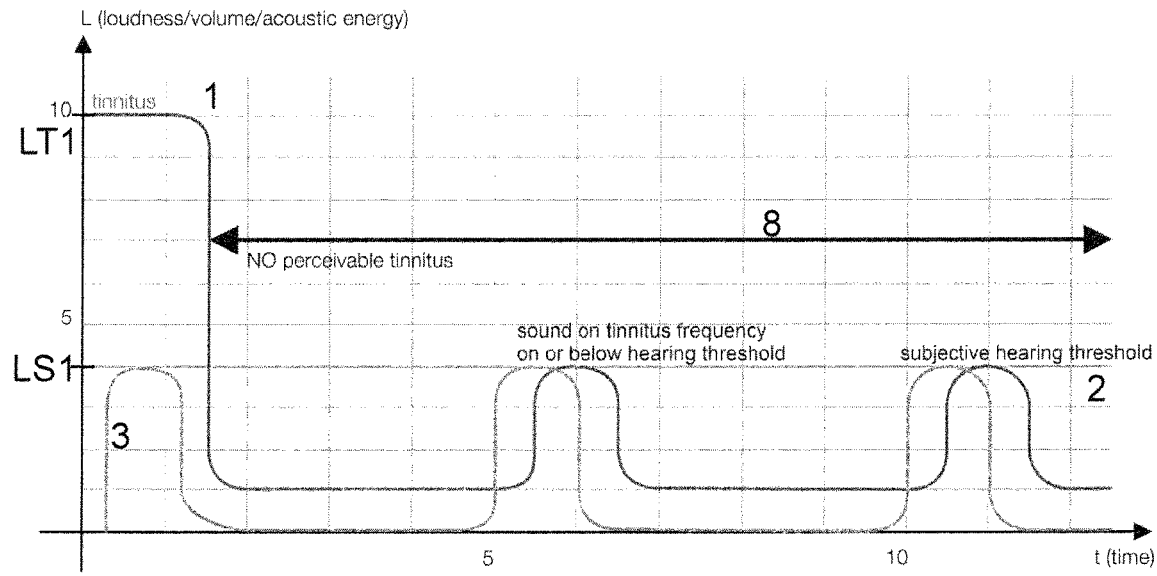

FIGS. 12 and 13 show methods similar to FIG. 9, i.e. with an intermittent sound 3 whose peaks have equal loudness LS1, but the loudness LS1 is lower than the original tinnitus loudness LT1. As discussed in the context of FIGS. 5 to 8, a reduction of loudness at frequencies around the tinnitus frequency fT is achieved even during the sound peaks. The method of FIG. 12 leads to periods of no cumulative sound between the peaks, whereas in FIG. 13 the tinnitus suppression is continuous since the peaks are not consciously perceived.

Figure 14:
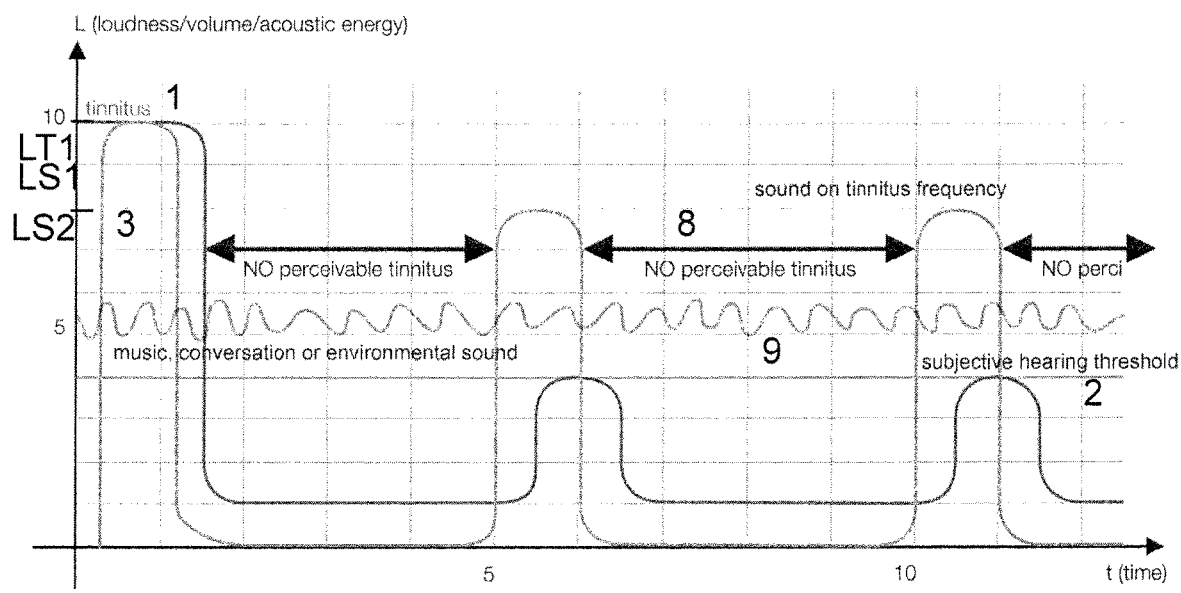

FIG. 14 shows a similar method as FIG. 10. However, at the same time with sound 3, also other sounds 9 are played to the user. The other sounds 9 may e.g. be music, a conversation or environmental sounds. The effect of the method is still achieved, the tinnitus 1 is suppressed. The method may, however, be more pleasant for the user, if other sounds 9 are present as well, e.g. a favorite piece of music. Besides, FIG. 14 illustrates that the method of the invention also works in noisy environments. Hence such method may easily be integrated into the every-day life of the user, which is an important prerequisite for success in practice.

In conclusion, the methods of FIGS. 9 to 14 produce an immediate and prolonged reduction 6 of loudness at the tinnitus suppression frequency, in particular the tinnitus frequency fT, i.e. the user's subjective tinnitus loudness plus sound 3 simulating the tinnitus, of up to 96% to 100%. A reduction of 100% is reached, if the sound 3 has a loudness LS1 on or below the hearing threshold 2, and if an interval of intermittency is equal to or shorter than the user's individual tinnitus deletion time 5. A reduction of 97% to 99% is reached, if the loudness LS1 is below the subjective tinnitus loudness LT1 but above the hearing threshold 2. A reduction of >93% is reached, if the loudness LS1 is equal to tinnitus loudness LT1, depending on the duration of the intermittent peaks and the interval of intermittency.

Figure 15:
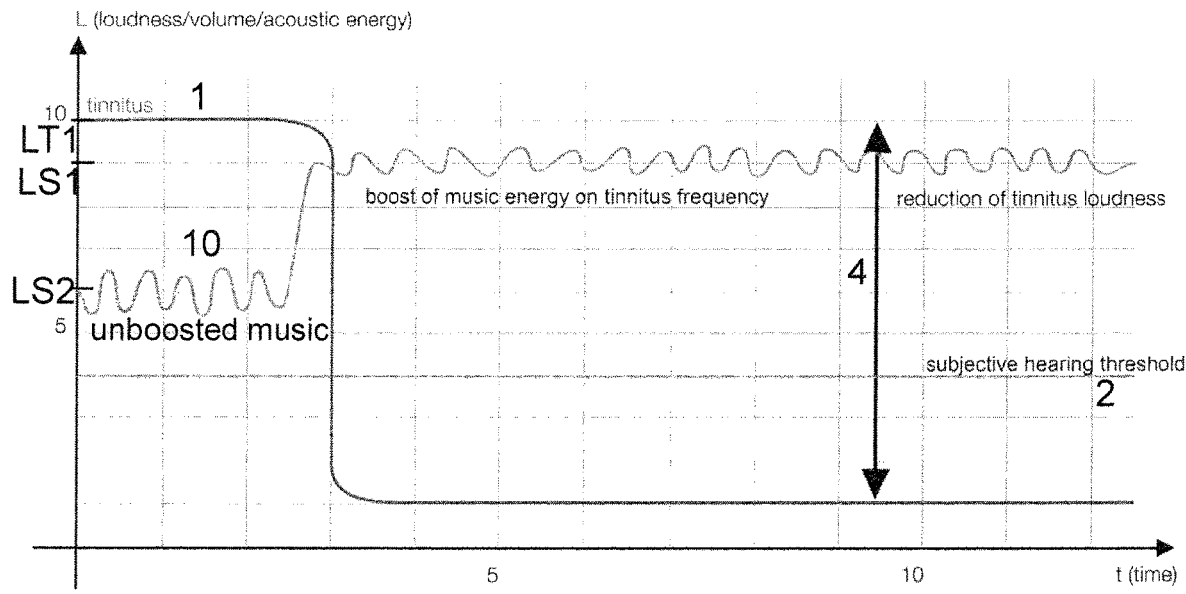
Figure 16:
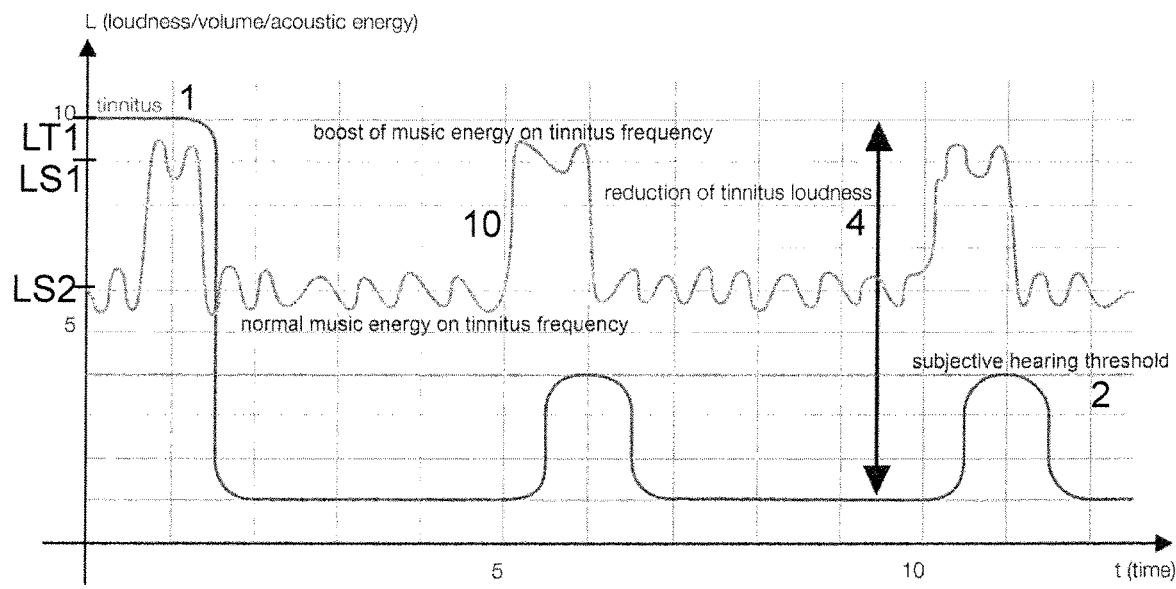
Figure 17:
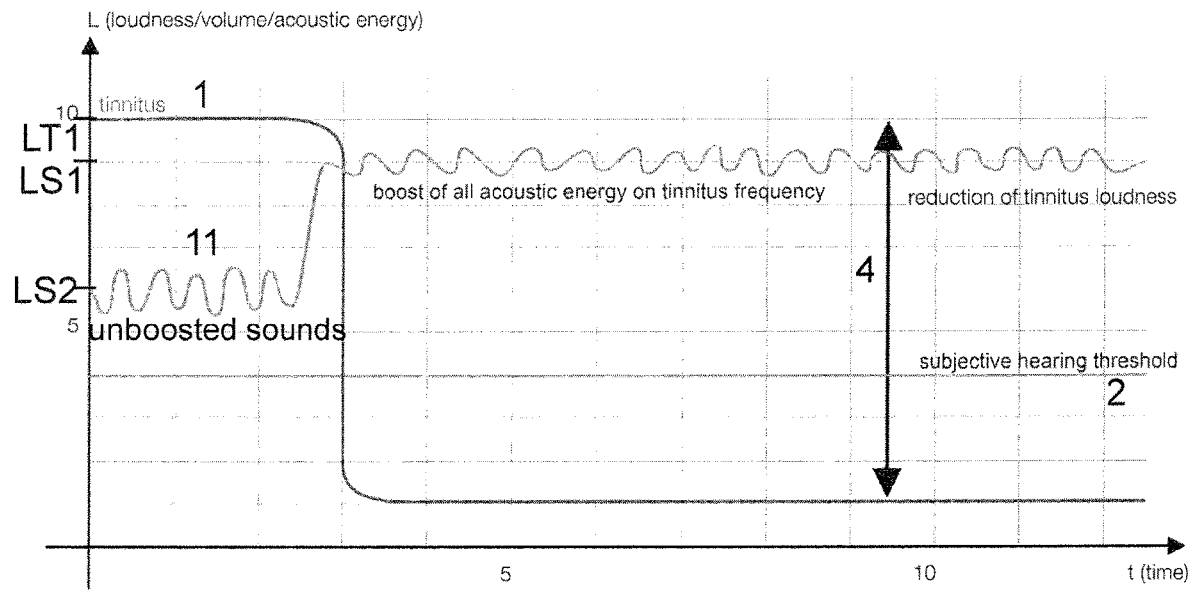
Figure 18:
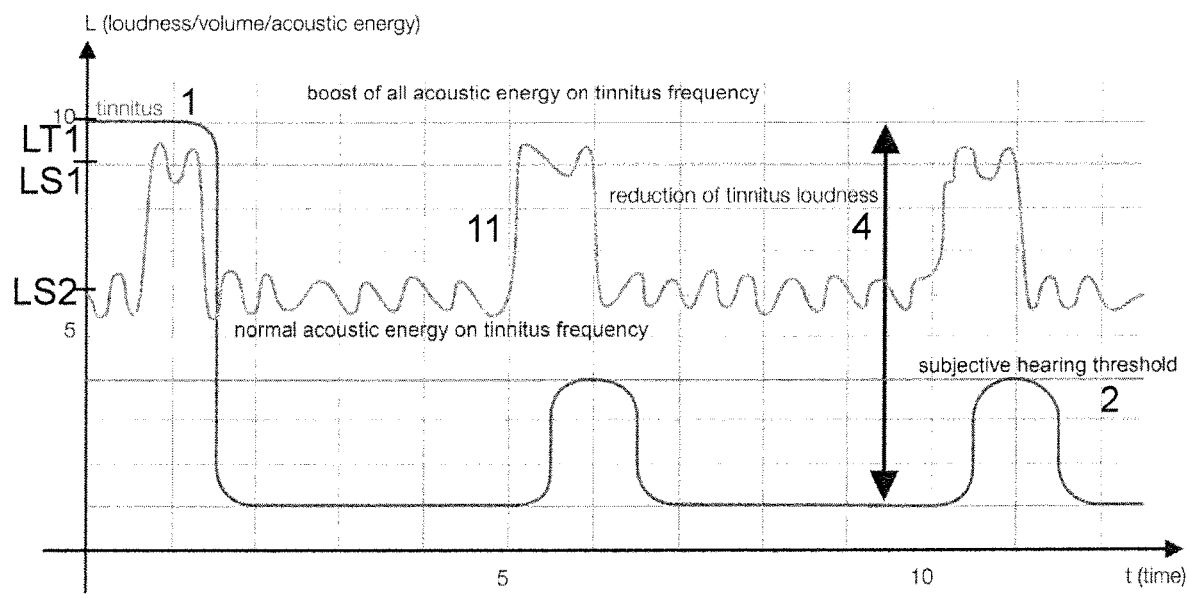

FIGS. 15 to 18 show time diagrams of methods with boosted music or boosted sounds according to embodiments of the present invention. Instead of using specifically created sounds in tinnitus suppression, such as a sinus sound or a tinnitus-like sound as in the above methods, it is also feasible to use other sounds whose frequency spectrum is adapted. Frequencies of the other sounds are boosted, i.e. increased in intensity e.g. by at least 25%, 50% or 100%, in a frequency range similar to the tinnitus suppression frequency, in order to get boosted music 10 (FIGS. 15 and 16) or a boosted other sound 11 (FIGS. 17 and 18). This may be achieved by bandpass filtering or by any way of increasing the acoustic energy at these frequencies by an analogue or digital program or apparatus. Alternatively, frequencies not fulfilling the criterion of being similar to the tinnitus suppression frequency may be attenuated or cut out, e.g. by at least 25%, 50% or by 100%, in order to achieve a similar effect on the user's tinnitus.

FIG. 15 represents the described method when using a continuous or permanent boost of music energy on or around the tinnitus suppression frequency. The boosted music has a first loudness LS1 at the tinnitus suppression frequency, which is smaller than the tinnitus loudness LT1, whereas an unboosted music has a second loudness LS2, which is smaller than the first loudness LS1 at the tinnitus suppression frequency. When the music that the unboosted music starts to be boosted, the tinnitus is suppressed below the hearing threshold 2 by the reduction 4 of tinnitus loudness. The user does not perceive the tinnitus 1 any longer but only the boosted music 10. Such method represents a pleasant tinnitus method since any favorite music of the user may be used. A prerequisite is that the unboosted music already contains acoustic energy in the frequency range to-be-boosted.

As can be seen from FIG. 16, the method of FIG. 15, i.e. the boosting of music in the frequency range of tinnitus or at octave shifts thereof, may as well be applied in an intermittent manner. During most of the time, the music is unboosted, i.e. it has normal acoustic energy in the relevant frequency range, in order not to disturb the usual sound characteristic of the music. For short intermittent pulses, e.g. of 1 s to 2 s length, the acoustic energy in this frequency range is boosted. This leads to a suppression of tinnitus 1 below the hearing threshold 2. The pulses are advantageously repeated at an interval equal to or shorter than the tinnitus deletion time 5, i.e. before the loudness of tinnitus 1 recovers to above the hearing threshold 2. In this way, the tinnitus is permanently suppressed without altering the pleasant impression of the music, i.e. its usual sound characteristic, for most of the time.

In an alternative embodiment, other sounds 11 in an environment of the user are boosted in the frequency range, in particular all other sounds which is the concept of FIGS. 17 and 18. This might e.g. be achieved by a hearing aid which the user wears anyway for reasons of hearing loss. If the user uses a hearing aid, the boost, i.e. the increase of acoustic energy, is performed on top of a correction which the hearing aid performs in that frequency range for compensating hearing loss. The boost may again be performed continuously (FIG. 17) or intermittently (FIG. 18). If a hearing aid is assumed to increase a loudness of sounds 11 in a frequency range of hearing loss up to 100% of an original hearing level, it increases the sound loudness in this frequency range above 100% of the original hearing level according to FIGS. 17 and 18, in particular to at least 125%, 150% or 200%. In this way, the tinnitus method may be integrated into the user's every-day life seamlessly and without any further effort or time requirements.

Figure 19:
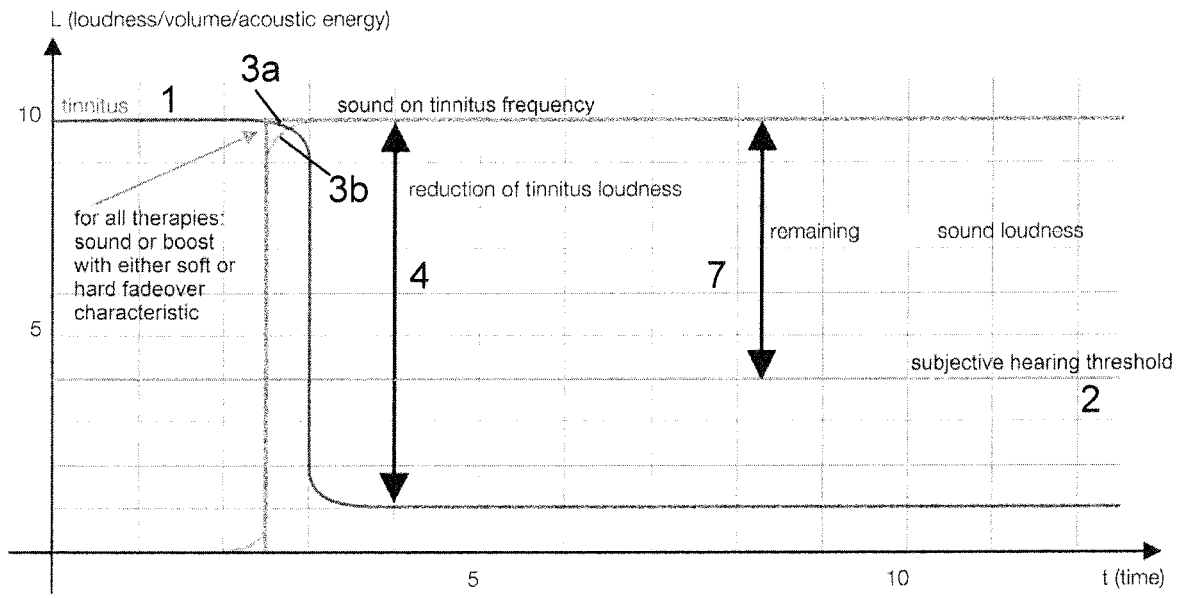

FIG. 19 shows a time diagram of different transition characteristics of the sound 3 played in a device or a method according to embodiments of the present invention. Two examples are given as sound 3a with an abrupt onset from zero loudness to LS1, and sound 3b with a smooth transition in loudness between zero and LS1. For the purpose of the method, the effect of both transition variants is the same: The tinnitus 1 is suppressed by the reduction 4 of tinnitus loudness below the hearing threshold 2. An abrupt transition, such as an abrupt onset of a sound or an abrupt onset of a boost, facilitates shorter sound pulses in a method with intermittent sound. Such abrupt transition may have the form of a step function, or it may comprise a slope of a short duration, such as e.g. shorter than 0.5 s or 1 s. A smooth transition, such as a fade-in and fade-out in form of a ramp, is e.g. a slope of a duration longer than 0.5 s or 1 s, may be more enjoyable for the user, in particular if the frequency spectrum of music or other sound is altered or boosted. Both forms of transition shown in FIG. 19 can be combined with various of the methods according to FIGS. 2 to 18.

Figure 20:
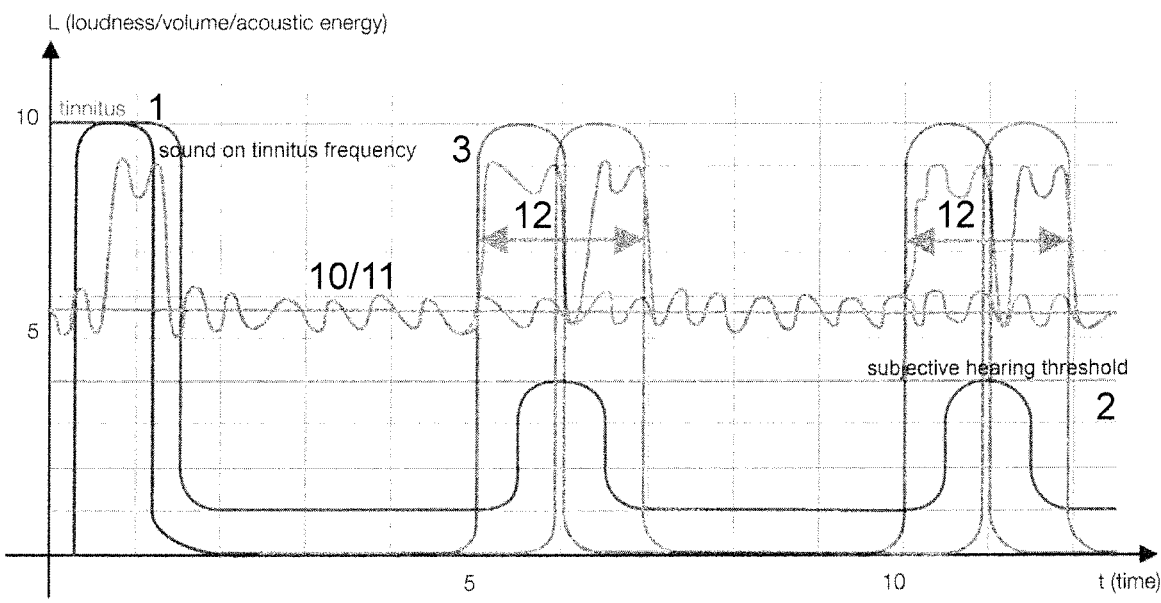

FIGS. 20 to 24 show time diagrams of an influence of an interval of sound intermittency or alternation on a degree of tinnitus suppression according to embodiments of the present invention. In FIG. 20, the interval of intermittency of the sound 3, and the interval of alternation of the boosted music 10 or of the boosted other sound 11 are varied by a small amount of variation 12 around the time of tinnitus deletion 5. It is clear that such variation 12 does not inhibit the effect of tinnitus suppression as long as the interval of intermittency or alternation is shorter than or equal to the time of tinnitus deletion 5. In that case, a subsequent sound 3 or boost pulse of music 10 or of other sound 11 will always suppress the tinnitus 1 again before its loudness increases above the hearing threshold 2.

Figure 21:
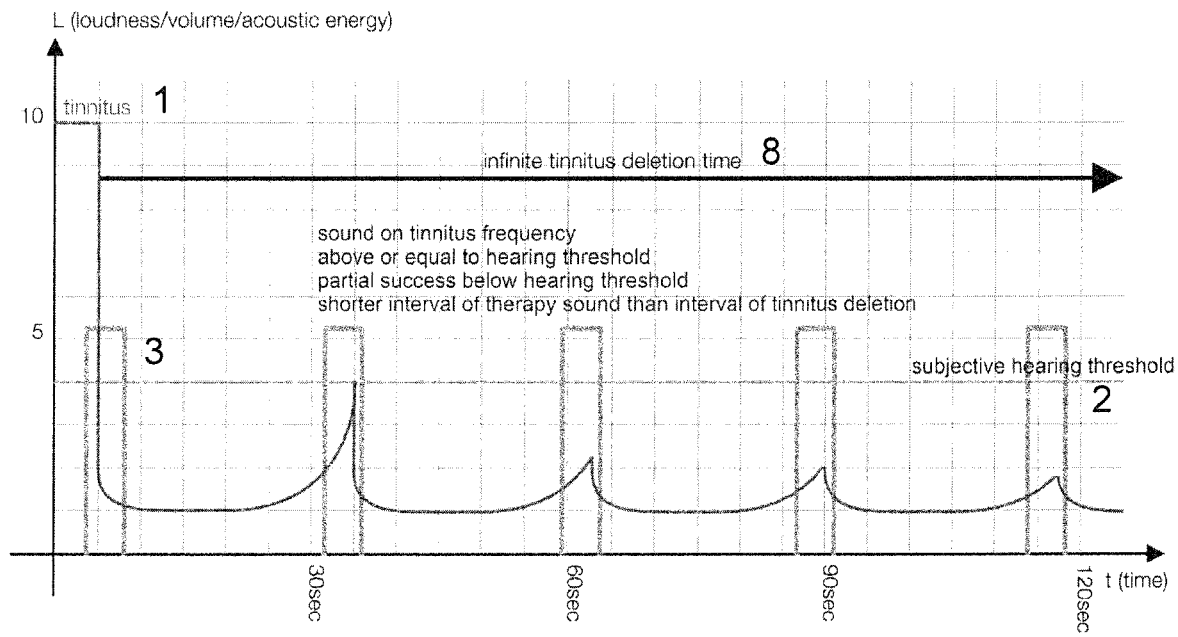

The situation of the interval of sound intermittency or alternation being shorter than the time of tinnitus deletion 5 is depicted in FIG. 21. The pulses of sound 3 with a frequency spectrum similar to the tinnitus suppression frequency suppress the tinnitus 1 before its loudness reaches the hearing threshold 2. Hence the perceived tinnitus deletion time 8 is theoretically infinite. The user may have heard pulses more frequently than necessary but this in uncritical to the success of the method. As mentioned before, partial success is also achieved, if the loudness LS1 of the sound pulses is below the hearing threshold 2, such that the user does not perceive them.

Figure 22:
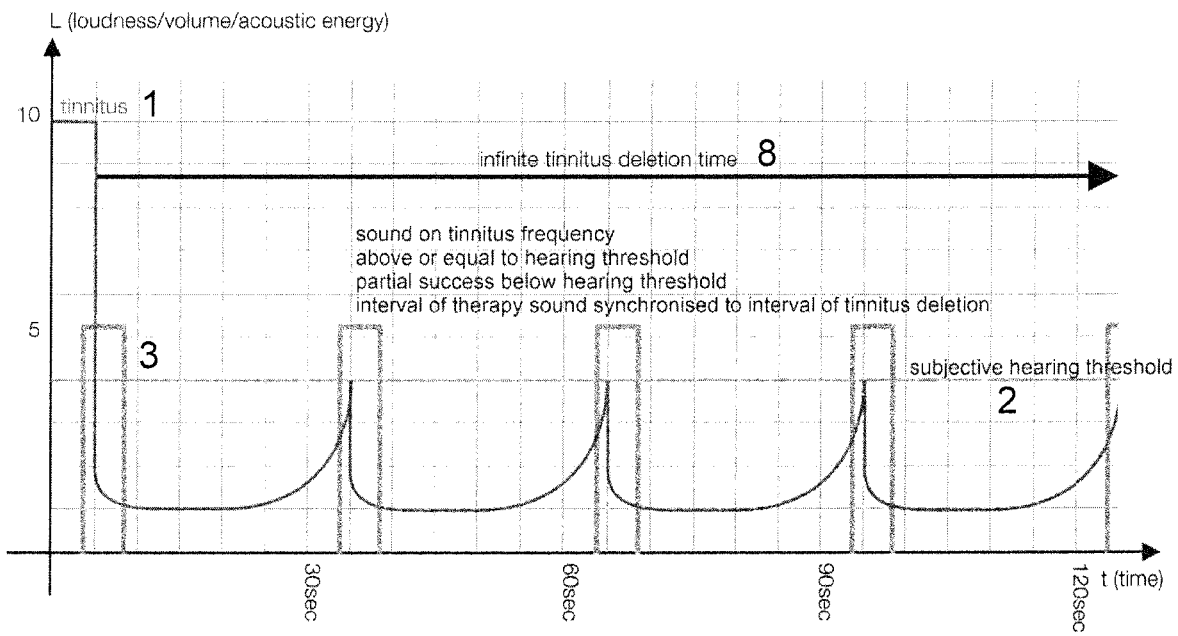

FIG. 22 depicts the situation of the interval of sound intermittency or alternation being equal to the time of tinnitus deletion 5. The two intervals are synchronized which also leads to a perceived infinite tinnitus deletion time. This is the optimal case since the user does not have to listen to more pulses of sound 3 or boosts of music 10 or of other sound 11 than necessary. For greater efficiency of tinnitus suppression, the first pulse of sound 3 displayed at around 5 to 10 s may be louder than the subsequent pulses, in particular louder than the loudness of the tinnitus 1 by 0 to 20 dB.

Figure 23:
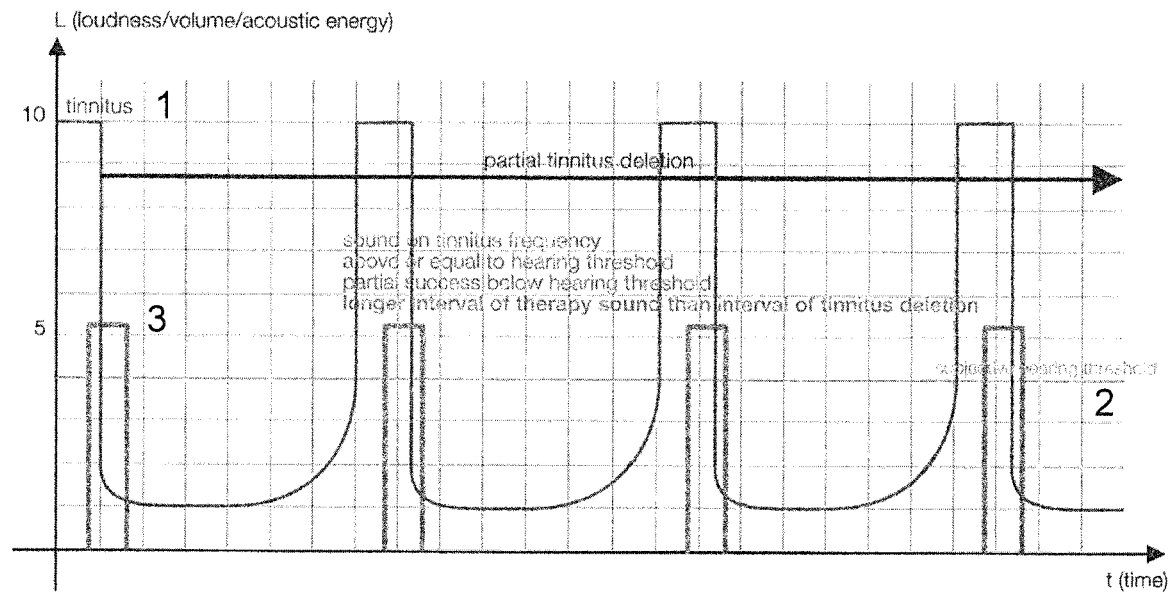

However, if the interval of sound intermittency or alternation becomes longer than the time of tinnitus deletion 5, the tinnitus 1 recovers with its loudness above the hearing threshold 2 for some time as shown in FIG. 23. Such behavior is not critical to the longterm effect of the method, which is a restructuring of the faulty neurons related to the tinnitus frequency fT. But it may be disturbing for the user since he/she repeatedly perceives the tinnitus 1 for some time before it is suppressed again.

Figure 24:
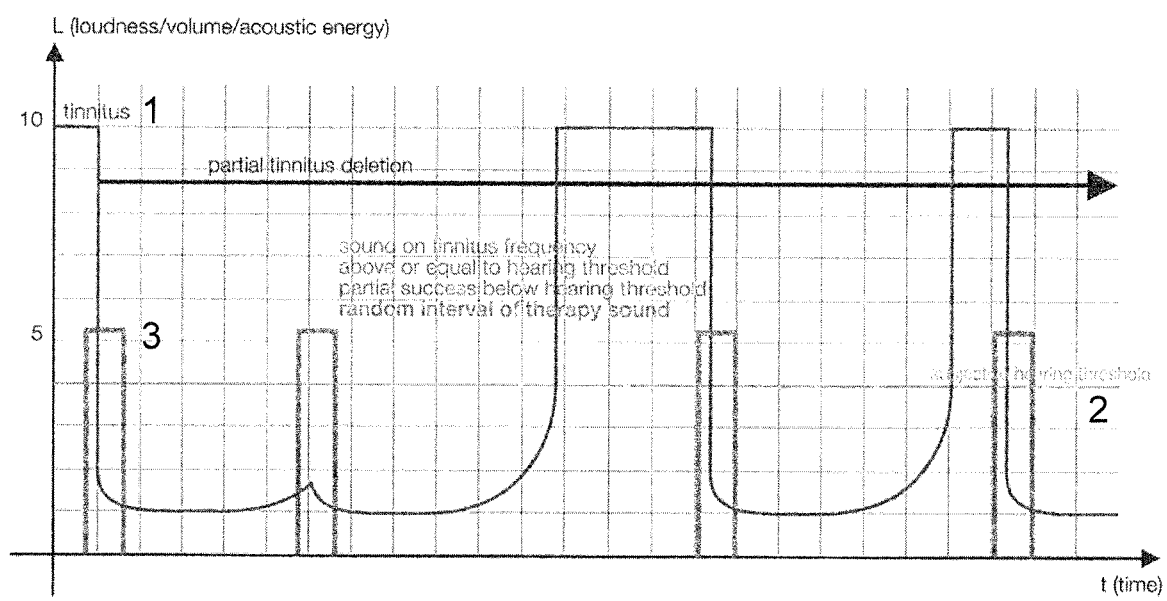

FIG. 24 shows pulses of sound 3 with random intervals of intermittency between them. In some cases, the user will not perceive the tinnitus 1 similar to FIGS. 21 and 22, while in others, the tinnitus 1 may even reach its original loudness LT1 before it is suppressed by a subsequent sound pulse. In this case, the user experiences a partial tinnitus deletion over time. The degree of tinnitus deletion over time depends on a probability distribution of the random intervals of intermittency. A method with such random interval of sound intermittency or alternation by boosts may be desirable because of its unpredictability, such that the user does not get used and bored by a regular interval, especially in the case of boosting music.

As is understood from the above description and figures, it is a general goal of the invention to relieve a user from the tinnitus, which may be perceived as painful and disturbing. An effect of the described device is that the tinnitus is suppressed or deleted in a convenient and easy-to-apply way, which leads to longer use times of the device and thus better success in tinnitus suppression. Another effect of embodiments of the device m is that they are not obtrusive for the user. This is true for the device itself, comprising e.g. a mobile phone, earphones or a hearing aid, as well as for its application.

The embodiments of the invention shown in FIGS. 25-28 show these advantageous effects to an even greater extent. This is achieved by tailoring the audio signal that is played to the user by means of determining at least one parameter regarding the user's tinnitus, and then modifying or generating the audio signal according to the at least one parameter. Examples for the parameter have been listed above and are described in the following. In general, it is advantageous that the at least one parameter may be determined with the device by the user alone, i.e. without the help of a trained person, e.g. a doctor or an audiologist, though assistance of a trained person is not excluded. Also, it is advantageous that the determination of the at least one parameter is repeated, e.g. in a regular interval of e.g. one week or month, or as soon as a change of parameters may occur. The at least one re-determined parameter is then automatically taken into account by the device for modifying/generating future audio signals.

Figure 25:
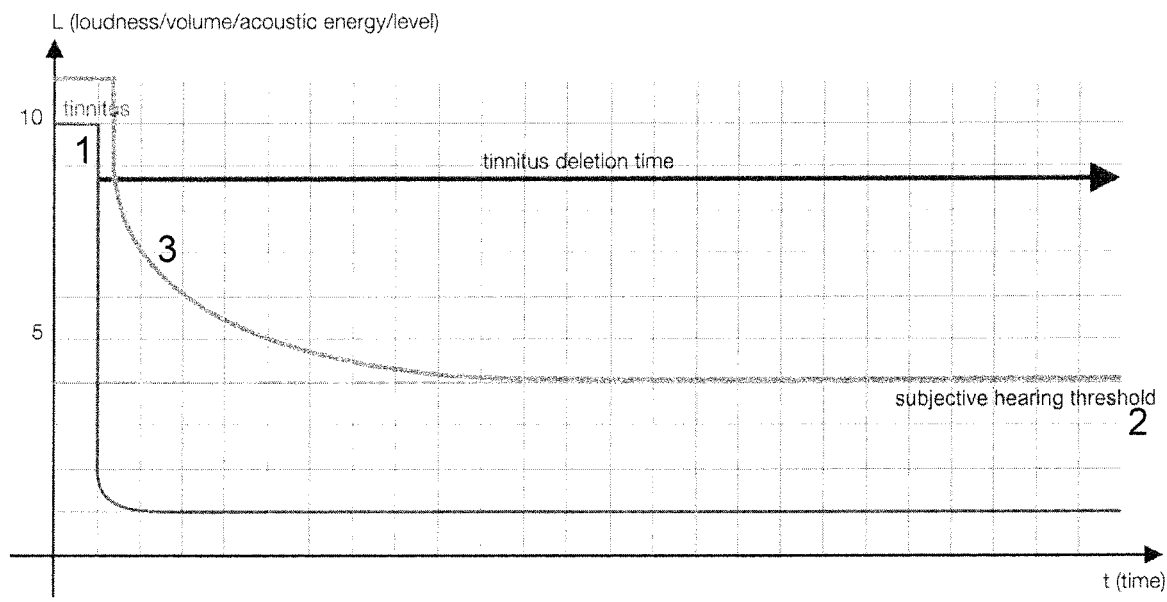

FIG. 25 shows that the sound 3 decreases in loudness over time and in particular as the loudness of the tinnitus 1 decreases. The evolution of the loudness of the sound 3 is adapted due to user feedbacks and re-determination of parameters over time. It is e.g. possible that the loudness of the sound 3 in general decreases over time according to a certain function, e.g. linearly or exponentially, e.g. by 5 dB per week, starting from an initial loudness of e.g. 90 dB. Advantageously, the user n presses a button on the device as soon as he/she starts to perceive the tinnitus again. In response to this user input, the loudness of the sound 3 is increased again, e.g. by a predefined amount, e.g. 5 dB.

In general, the evolution of the loudness of the sound 3 does not have to be monotonically decreasing as in FIG. 25, but the loudness may also adapted to greater values, e.g. if the initial loudness of the sound 3 is not sufficient to suppress or delete the tinnitus. However, the advantage of the embodiment of FIG. 25 is the adaptation of the sound loudness to the minimum required loudness by measuring the latter over time.

In general, such embodiment with adapting loudness of the sound 3 has the effect that the sound is not (much) louder than necessary in order to suppress the tinnitus, i.e. the sound is played with a loudness just above the minimum suppression sound loudness. Note that the minimum suppression sound loudness may be above, at or below the hearing threshold. In this way, the sound is less disturbing or obtrusive to the user.

Figure 26:
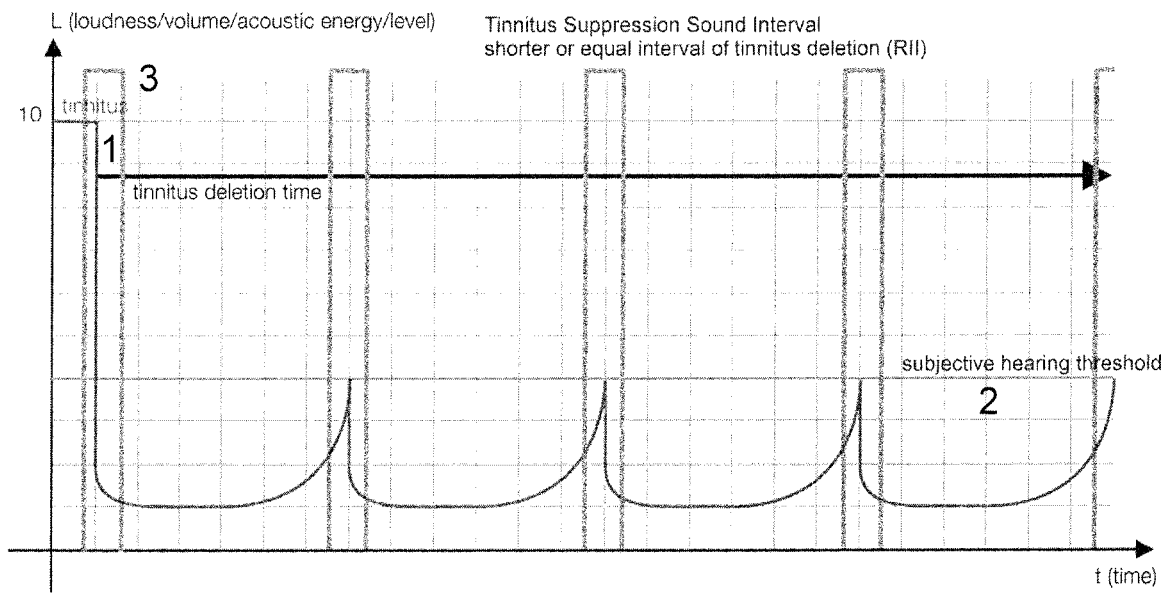

FIG. 26 shows the temporal evolution of the sound 3 when a different parameter, in this case the tinnitus suppression sound interval, i.e. the interval between subsequent pulses of sound 3, is adapted. For the user not to perceive the tinnitus 1, the tinnitus suppression sound interval should be shorter or at most equal to the interval of tinnitus deletion. As there may be changes of this parameter over time in a user, the interval of tinnitus deletion is re-determined and the sound 3 is adapted to its new value.

Figure 27:
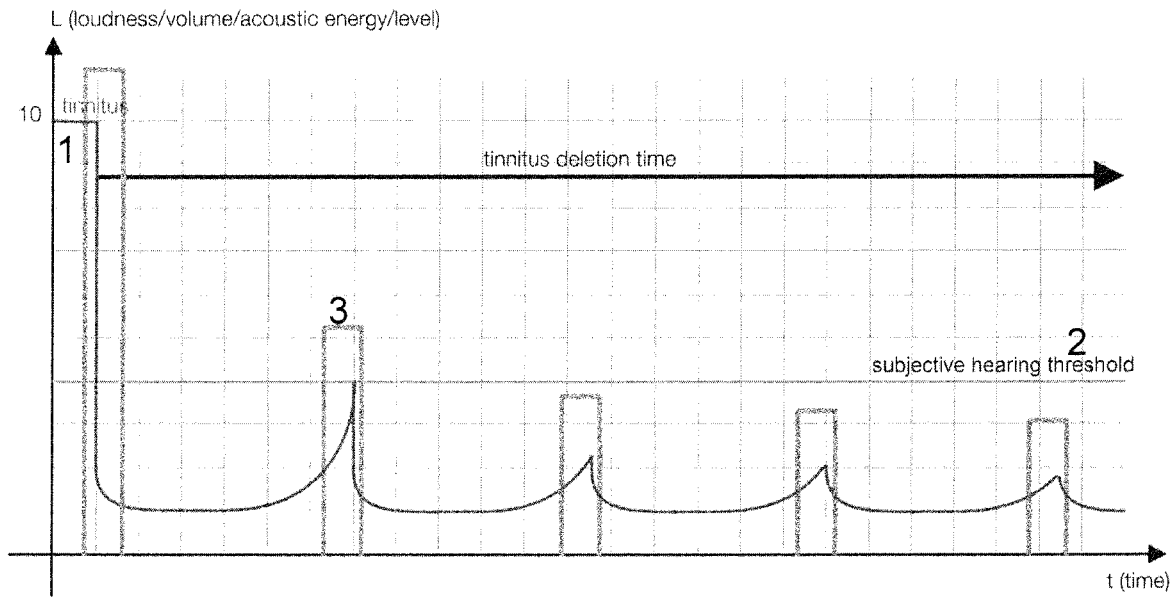

FIG. 27 depicts the situation in which the loudness of the sound 3, in this case an intermittent sound, is adapted over time. As in FIG. 25, the adaptation of the loudness is advantageously in response to a change of the minimum required loudness or a change of tinnitus loudness. In particular, the parameter minimum required loudness or tinnitus loudness is re-determined after a certain time, and the sound loudness is adapted for an optimum tinnitus suppression, which at the same time is least obtrusive for the user. This embodiment may be combined with the re-determination and adaptation of the interval of tinnitus deletion described above for FIG. 26.

Figure 28:
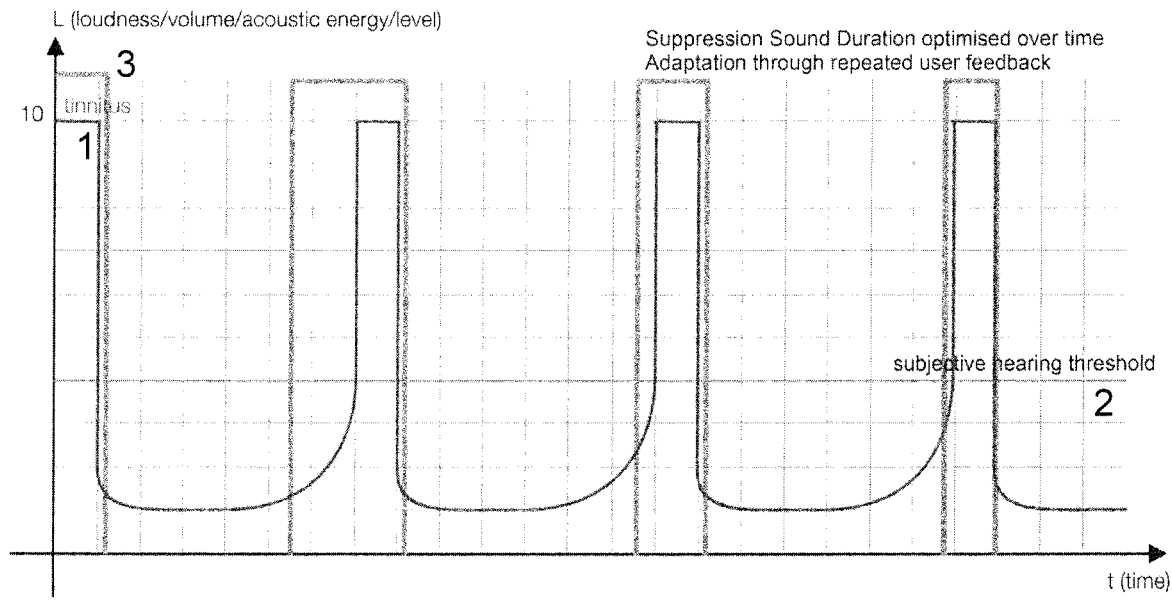

In the embodiment of FIG. 28, the duration of the sound 3, in particular of pulses of sound, is adapted over time according to user feedback. This may be desired in order to reduce the obtrusiveness or disturbance from the signal to the user. By adapting the sound duration to repeated user feedback, the sound duration preferably approaches the minimum suppression signal duration, e.g. asymptotically, for which tinnitus suppression or deletion is still achieved. Advantageously, the adaptation of the sound duration, in particular the determination of a minimum required sound duration for tinnitus suppression, is performed after other parameters such as the tinnitus suppression frequency and the minimum required loudness have been adapted.

In a similar way, an embodiment of the device offers the possibility to adapt the sound quality to the user's present preferences. Sound quality may be influenced by the type of sound 3 played, e.g. sinus sound, noise, instrumental music, pulsating sound, or by a frequency characteristic. In such way, the user can choose the least obtrusive sound quality for his/her present situation, while still achieving tinnitus suppression or deletion.

In a similar way, an embodiment of the device supports an adaptation of the transition of the intermittent or alternating sound as described with respect to FIG. 19. Preferably a characteristic of the transition, such as a fade-in and/or fade-out duration, is adapted according to user feedback.

In a similar way, an embodiment of the device offers the possibility to change a distribution of the acoustic energy in the sound 3 within the defined frequency spectrum. In particular, this means that the sound at the tinnitus suppression frequency, in particular the tinnitus frequency fT, may be played with lower loudness while sounds at one or more octaves distance to the tinnitus suppression frequency are played with higher loudness. An example is lowering the loudness of the sound at 8000 Hz, while increasing the loudness at 4000 Hz and/or 2000 Hz and/or 1000 Hz. In this way, the sound may be made more pleasant according to user input. At the same time, this may be beneficial for the overall effect of tinnitus suppression since, in general, the tinnitus frequency fT often correlates with hearing loss in a similar frequency range, i.e. around fT.

Figure 29:
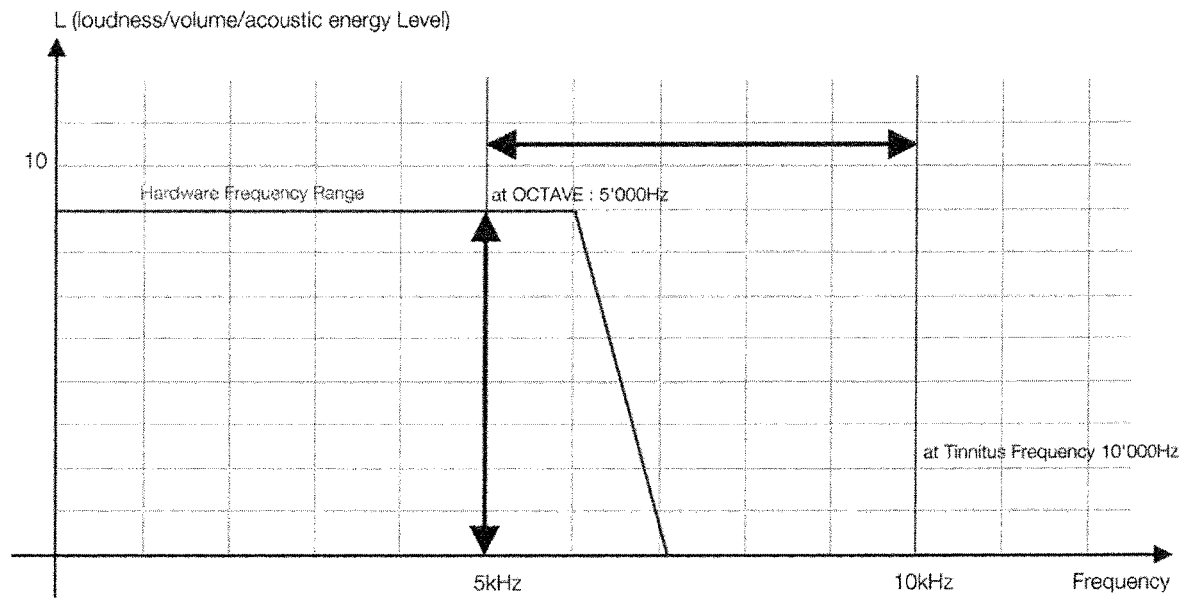
Figure 30:
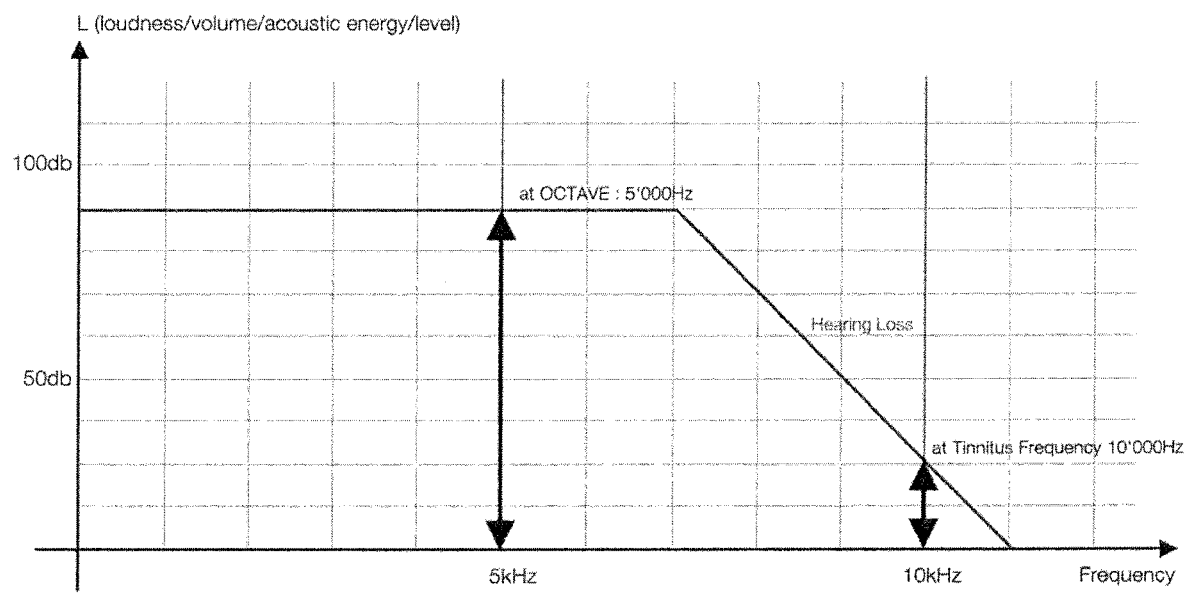
Figure 31:
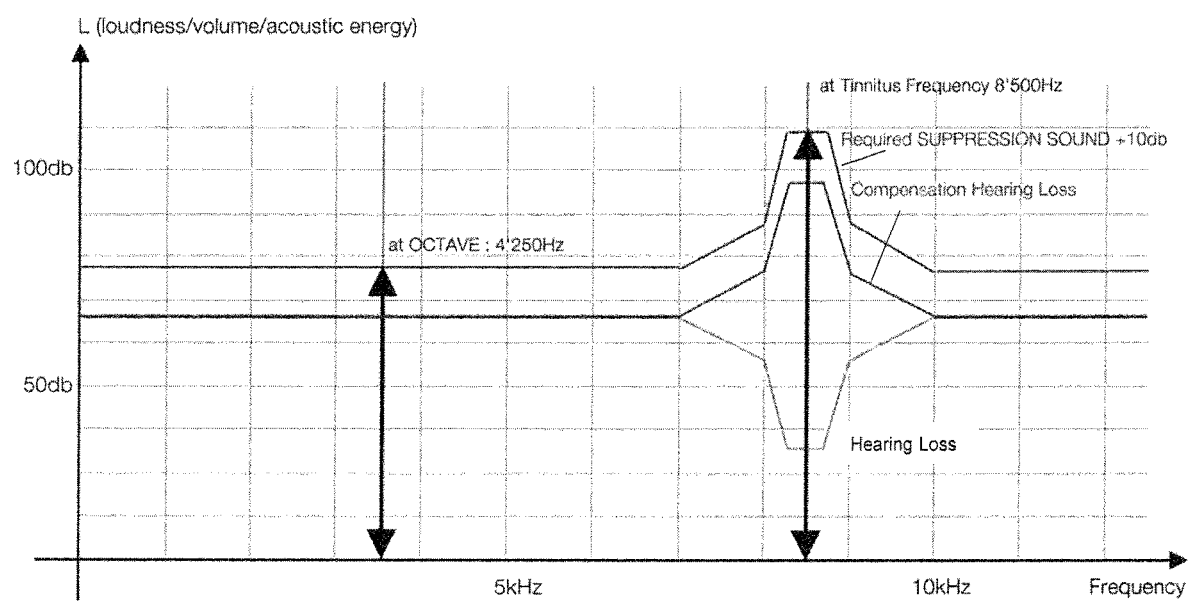

Some features that are advantageous, in particular in the case of the device being a hearing aid or comprising functions of a hearing aid, are shown in FIGS. 29 to 31.

FIG. 29 shows the frequency response of a certain device producing a sound, in particular a hearing aid, which is limited to frequencies below e.g. 6000 to 7000 Hz due to limitations of its hardware or software. If the tinnitus suppression frequency, in this case 10000 Hz is above this range and a tinnitus suppression sound shall be played at the tinnitus suppression frequency, the device does not actually play the sound, thus the effect of tinnitus suppression is not achieved. In such case, the tinnitus suppression sound is played at frequencies of the defined frequency spectrum which are one or more octaves lower than the tinnitus suppression frequency, see above, in particular at frequencies inside the range of frequencies supported by the hardware. If the tinnitus suppression frequency is below the capability of the hardware, the suppression sound is advantageously played at one or several octaves above the tinnitus suppression frequency.

A similar situation, in which octave-shifting of the acoustic energy in the suppression sound is useful, is shown in FIG. 30. A user may have normal hearing capabilities up to 7000 Hz but hearing loss above and a tinnitus at fT=10000 Hz. In this case, playing a sound at the tinnitus suppression frequency similar to fT is ineffective in terms of tinnitus suppression. Rather, the suppression sound is played one or more octaves lower than the tinnitus suppression frequency, e.g. at 5000 Hz. In this way, tinnitus suppression or deletion can still be achieved, even under severe hearing loss. This feature is particularly useful since studies show that the frequencies of tinnitus, of an optimum tinnitus suppression sound and of hearing loss often overlap. In reverse, this also applies to hearing loss at lower frequencies, e.g. below 100 to 200 Hz.

FIG. 31 shows a similar situation where a user has a tinnitus at fT=8500 Hz and additionally a significant hearing loss around this frequency, in particular in the range between 7000 Hz and 10000 Hz. While playing a sound at fT may still achieve tinnitus suppression to a low degree, the required loudness of the sound for suppression may be high and in particular so high that it is damaging to the user's ear. In the displayed example, the user's hearing loss at fT is 50 dB and the tinnitus has a loudness of 70 dB. Hence a conventional hearing aid will amplify sounds at fT by 50 dB, and in particular the tinnitus to 70 dB+50 dB=120 dB. According to studies, another 10 dB will be added for an optimally effective tinnitus suppression sound. Thus the suppression sound will be played at fT with 130 dB. This is unpleasant for the user and damaging to the ear.

A solution as depicted in FIG. 31 is playing the suppression sound at one or more octaves lower than fT, e.g. 4250 Hz, where the hearing of the user is better or normal. An optimum loudness of the suppression sound in that case is 70 dB+10 dB=80 dB. This is acceptable for the user, and damages to the ear are avoided.

FIG. 32*a-c* show examples of frequency spectra of sounds applied in methods according to embodiments of the present invention. They have been discussed in the context of FIG. 1, see above.

Figure 33:
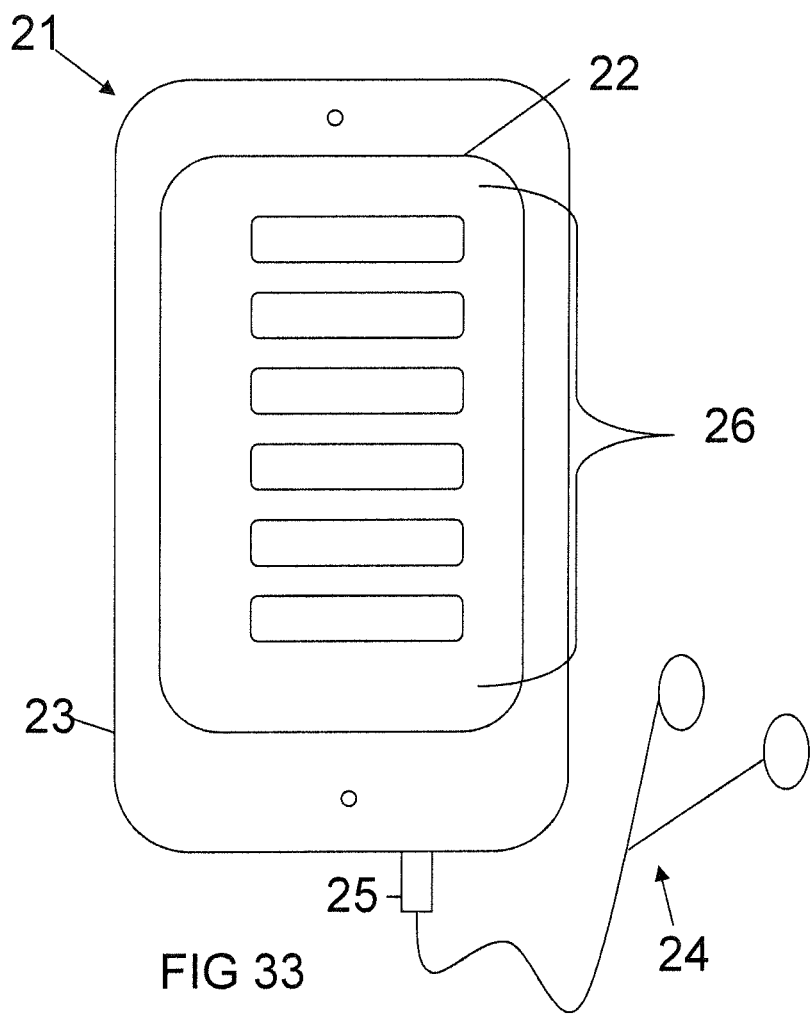

FIG. 33 illustrates a schematic view of a mobile phone according to an embodiment of the present invention. The mobile phone 21 is a smartphone comprising a display 22 which constitutes an interface 26 to the user. The mobile phone 21 i.a. contains a housing 23 and a plug 25 for earphones 24.

Figure 34:
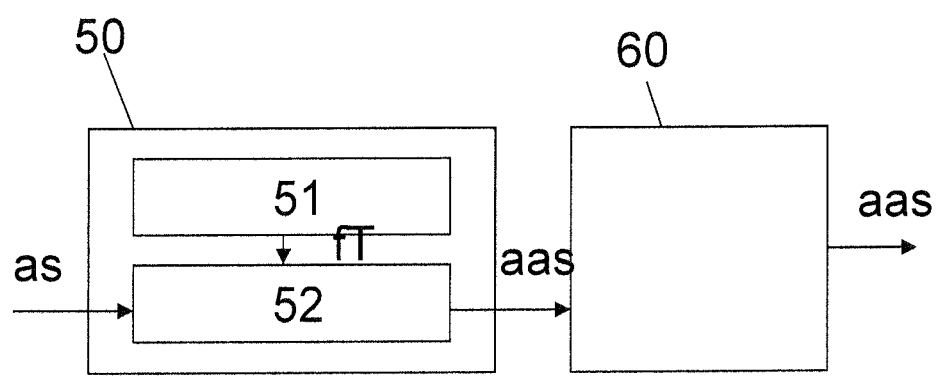

FIGS. 34 to 37 illustrate block diagrams of components of an electronic device according to embodiments of the present invention. In FIG. 34, a software engine 50 includes an identification unit 51 and an adaptation unit 52 both of which may act on an audio output unit 60. The identification unit 51 supports identifying, for example, a frequency fT and/or a loudness of a user's tinnitus. The tinnitus frequency fT and/or loudness is input to the adaptation unit 52 which converts the tinnitus frequency fT in a defined frequency characteristic, which in this specific embodiment is a filter characteristic, or builds a frequency characteristic based on the identified tinnitus frequency fT or loudness. Such frequency characteristic is applied by the adaptation unit 52 to an audio signal <as>, which preferably is stored in a memory of the apparatus. The filtered audio signal <as>, also called adapted audio signal <aas> is input to the audio output unit 60 for being played to the user. Playing the adapted audio signal <aas> may be initiated by triggering the process of modifying audio signal <as> accordingly, or may be initiated by a user independent from the building of the adapted audio signals <aas> at any later point in time.

Figure 35:
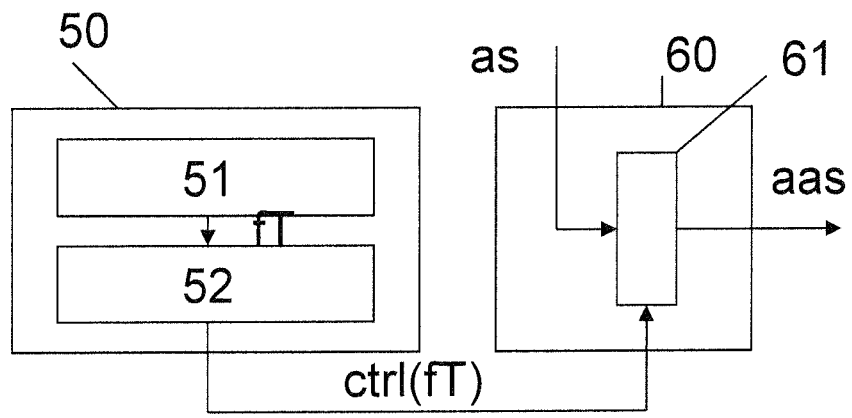

In the block diagram of FIG. 35, a different way is illustrated for adapting audio signals <as>. Such way may be denoted as "on the fly" adaptation in that a sound modifier 61 of the audio output unit 60 is controlled by the adaptation unit 52 by means of a control signal ctrl(fT) for implementing the frequency characteristic that is derived from the identified tinnitus frequency fT. The sound modifier 61 tunes the audio signal <as> while playing it accordingly such that the adapted audio signal <aas> may be played to the user by the audio output unit 60. In this embodiment, it may not be necessary to store the adapted audio signals <aas> in the electronic device, and only the audio signal <as> may be stored as is the frequency characteristic based on the identified tinnitus frequency fT.

FIGS. 34 and 35 may also be interpreted as a working mode of a hearing aid. In that case, external sound <as> is recorded by a microphone and transmitted to the adaptation unit 52 (FIG. 34), or the sound modifier (FIG. 35). There, the frequency spectrum of the external sound is modified, i.e. adapted according to the tinnitus frequency fT, e.g. as shown in FIG. 32*c*. In an embodiment, the adaptation of the external sounds according to the proposed tinnitus method is performed on top of a regular function of the hearing aid which rectifies a hearing in certain frequency ranges.

Alternatively, the audio signal <as> in FIG. 35 may be a generic sound, such as e.g. a sinus sound, which is generated by a sound generator or by the audio output unit 60 itself. The generic sound <as> is then adapted according to a frequency spectrum comprised in the control signal <ctrl (fT)> which is determined by the adaptation unit 52 based on the tinnitus frequency fT or loudness as determined by the identification unit 51.

In an embodiment, the identification unit 51 supports also a determination of the tinnitus deletion time and/or a determination of the hearing threshold, e.g. depending on the frequency. In that case, the audio signal <as> may additionally be modified or adapted according to the determined tinnitus deletion time and/or the determined hearing threshold by the adaptation unit (FIG. 34) or the sound modifier 61 (FIG. 35).

Figure 36:
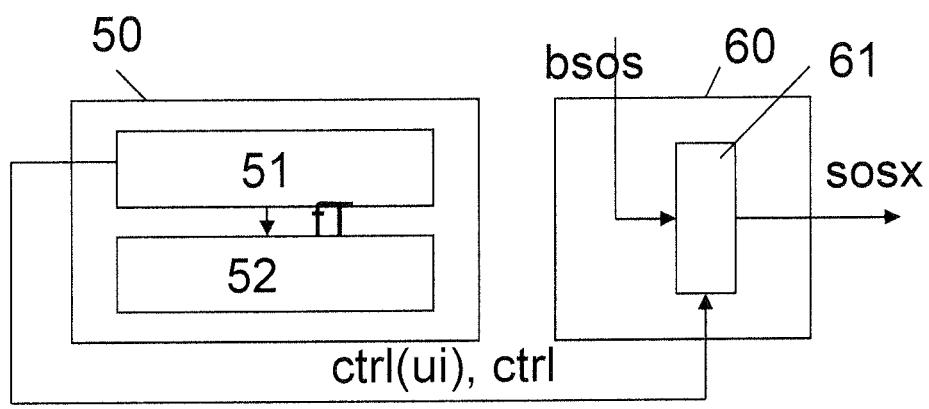

FIG. 36 shows another block diagram which focuses on the generation of sound samples <sosx> rather than adapted audio signals <aas>. A basic sound sample <bsos> may be stored in the device, and for supporting identification of the relevant tinnitus frequency fT, the identification unit 51 controls a sound modifier 61 of the audio output unit 60 by control signal <ctrl(ui)> for generating a sound sample <sosx> out of a basic sound sample <bsos>. The control signal <ctrl(ui)> is subject to the user input <ui> which may denote a modification such as frequency up or frequency down with respect to the most recent sound sample <sosx> played. The identification unit 51 translates such user input <ui> into the control signal <ctrl(ui)> for adjusting the sound modifier settings for, for example, generating a sound sample <sosx+1> from basic sound sample <bsos> that has a higher tone than the previous sound sample <sosx> played. In an alternate embodiment, a control signal <ctrl> makes the sound modifier 61 play sound samples <sosx> in a defined order. In another advantageous embodiment, the next sound sample <sosx+1> differs from the sound sample <sosx> in loudness such that a perceived loudness of the tinnitus may be determined. In a similar way, it is possible to determine the hearing threshold, or the tinnitus deletion time of the user. Alternatively and in general, the tinnitus suppression frequency is determined and used instead of the tinnitus frequency fT.

Figure 37:
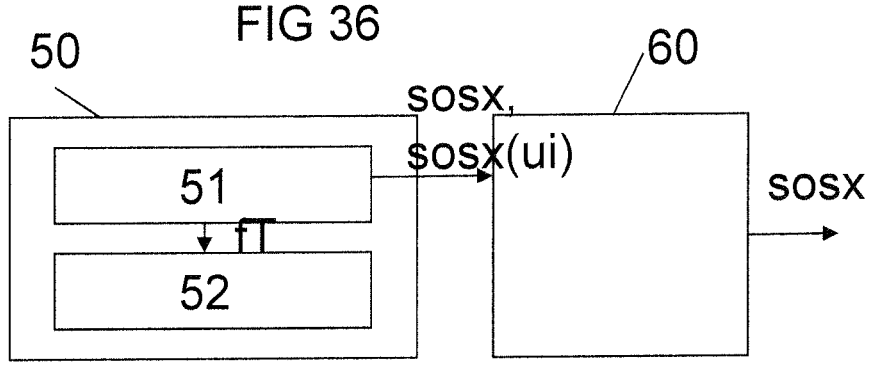

FIG. 37 illustrates another block diagram which focuses on the generation of sound samples <sosx>. In this example, the apparatus holds multiple different sound samples <sosx> that can be selected for being played by the audio output unit 60 by the identification unit 51. The selection may follow a defined order of n sound samples <sosx>, e.g. by rising frequency, or may depend on the user input <ui> which may be translated by the identification unit 51 into the right choice of sound sample <sosx(ui)> to be played next.

Figure 32:
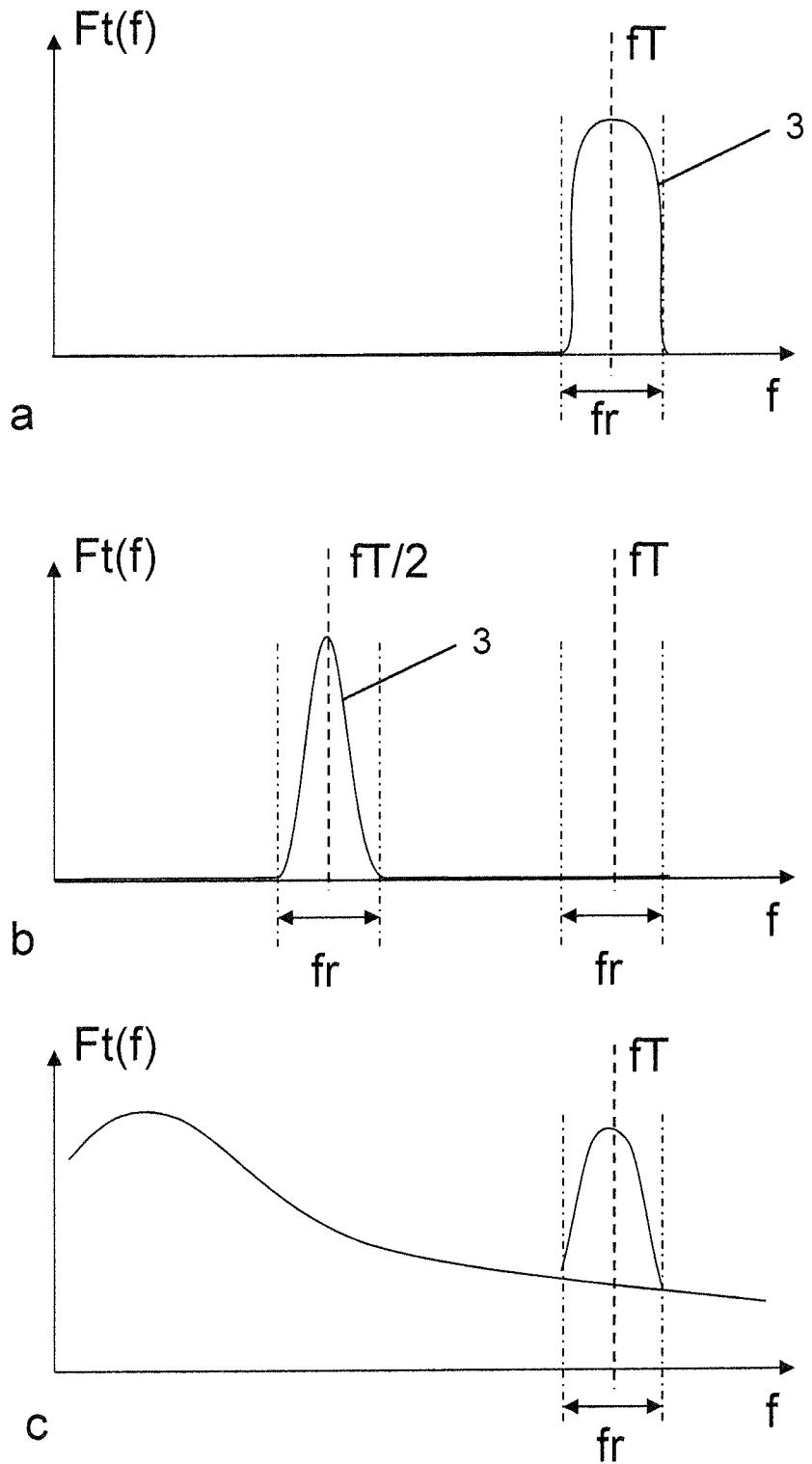

Once the tinnitus frequency fT is determined, a frequency characteristic of the one or more selected audio signals as may be adapted according to the tinnitus frequency fT determined. Sample frequency characteristics Ft(f), to be applied to an audio signal as, are shown in FIG. 32 and were described above in the context of FIG. 1.

It is appreciated, that such modification to the frequency characteristic is not limited to an adaptation in the high frequency range but may also be applicable to low or medium portions of the audible frequency range. Any such adaptation/modification applied may either increase or lower associated frequencies. By means of adapting the frequency characteristic also outside the frequency range identified, other auditory disorders may be addressed such as hearing loss. For identifying such other auditory disorders, the present apparatus may be used, for example, as a device for identifying such other auditory disorders. In a preferred embodiment, the apparatus may be adapted for executing an audiometry. In such audiometry, sound samples representing different frequencies may be played to the user via the audio output unit. The user is requested to indicate via a suitable interface—e.g. by pressing a button—the point in time he/she hears the sound sample. Summarizing the user's responses over the audible frequency range delivers an audiogram of the user indicating his/her hearing capability in form of hearing loss. Out of such information, the present apparatus may automatically identify frequencies or frequency ranges to be adapted, and in particular to be one of amplified or attenuated. Such frequency ranges may accordingly be adapted in the frequency characteristic that will be applied to the audio signals.

Figure 38:
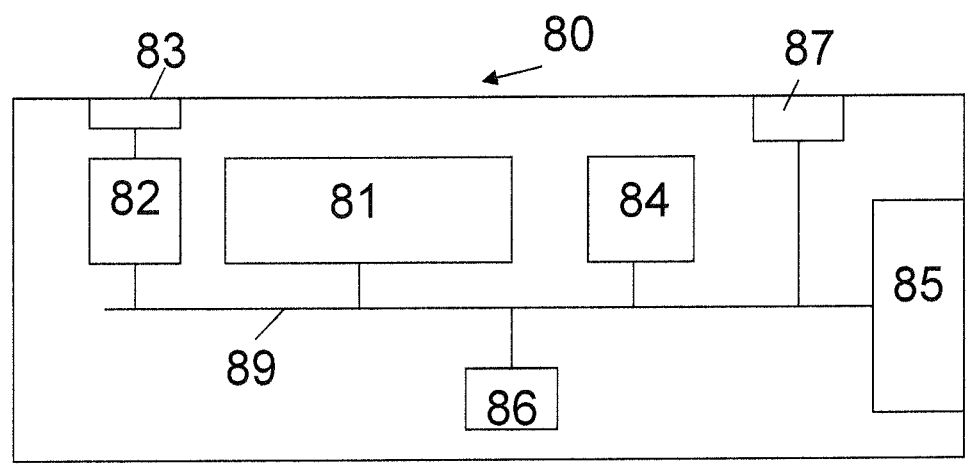

FIG. 38 shows a block diagram of an electronic device according to an embodiment of the present invention, and specifically of a mobile electronic device 80, in a more hardware oriented manner than in block diagrams in FIGS. 34 to 37. The electronic device includes a processing unit 81 which is connected via an internal bus 89 i.a. to a non-volatile memory 84, such as a ROM, which may be implemented, for example, in Flash technology, and to a volatile memory 86, such as a RAM, which may, for example, be implemented in DRAM technology. Reference sign 85 denotes a wireless interface such as a 4G interface for transmitting and receiving data in a wireless manner. The electronic device 80 further includes a digital/analogue converter 82 for supplying an audio output 83 with analogue audio signals. In addition, the electronic device 80 supports a user interface 87 which may be a graphical user interface including a display and some input means.

For example, the wireless interface 85 may be used for receiving audio signals from a provider. The 3o user interface 87 may support selection and downloading of audio signals via the wireless interface 85. The audio signals may be stored in the non-volatile memory 84. In the non-volatile memory 84, a computer program element may be resident which supports identification of a frequency range of a user's auditory disorder, which allows deriving a frequency characteristic from the identified frequency range, which applies the frequency characteristic to a selected audio signal for generating an adapted audio signal, and which finally supports playing the adapted audio signal. Such computer program element may be loaded into the volatile memory 86 by the processing unit 81 for being executed.

In this context, the user interface 87 may be involved requesting for user input related to the frequency range that matches the tinnitus perception best. In one embodiment, sound samples may be output to the user. Such sound samples may be stored in the non-volatile memory 84 and be output via a D/A converter 82 to the audio output 83 which may be a plug for earphones, for example. Once the frequency range is determined, the processing unit 81 may store this information in one of the memories 84, 86 and may generate, in a specific embodiment, a filter characteristic based on the frequency range. The filter characteristic may be stored in any of the memories 84, 86, and be applied to an audio stream representing an audio signal being loaded for being played via the components 82 and 83.

Figure 39:
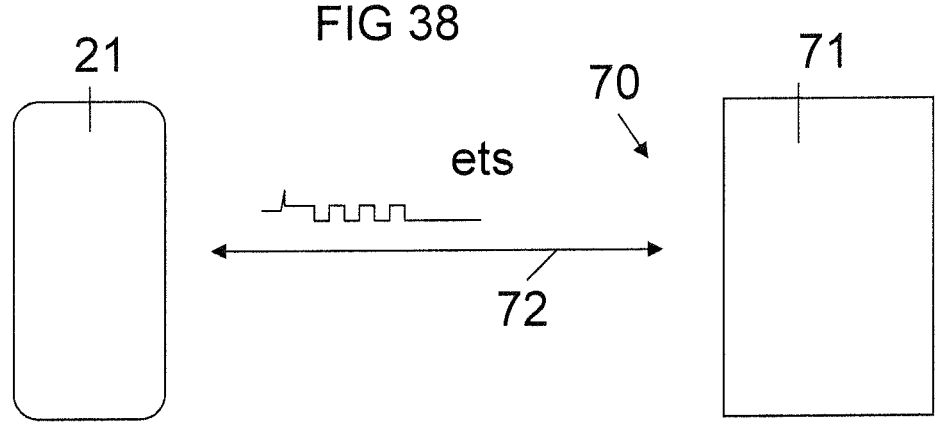

FIG. 39 shows a system 70 for downloading a computer readable element as may be used with the mobile phone 21. The system may include a server 71 including storage means. Reference sign 72 indicates a transmission network, such as the internet. A mobile phone 21 receives the computer readable element, also called "app" in this context, which during transmission is represented by an electrical transmission signal <ets>.

Figure 40:
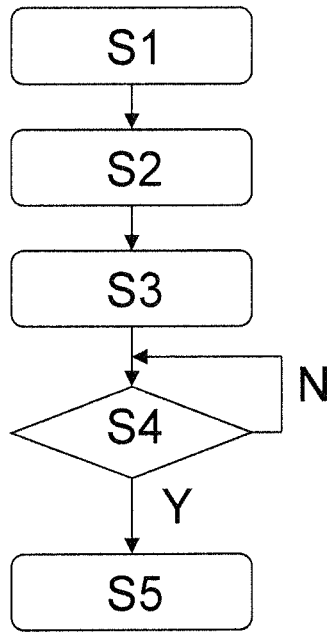

FIG. 40 shows a flow chart of part of a method of the present invention. In step S1, the method is started, e.g. by pressing an icon representing the "tinnitus app" on the mobile electronic device. In step S2, the "app" supports identification of a tinnitus suppression frequency associated with an auditory disorder of a user of the mobile electronic device, such as referred to in previous embodiments. Alternatively or additionally, the "app" supports a determination of one or more further quantities such as tinnitus loudness, tinnitus deletion time and hearing threshold. In step S3, a frequency characteristic of an audio signal, e.g. representing a track of music, is adapted subject to the identified tinnitus suppression frequency and to the further determined quantities. In step S4, the electronic device waits for a user input to start playing the adapted audio so signal. If such input is received (Y), the adapted audio signal is played. If it is not received (N), the process may wait for any such input in the future.

Figure 41A:
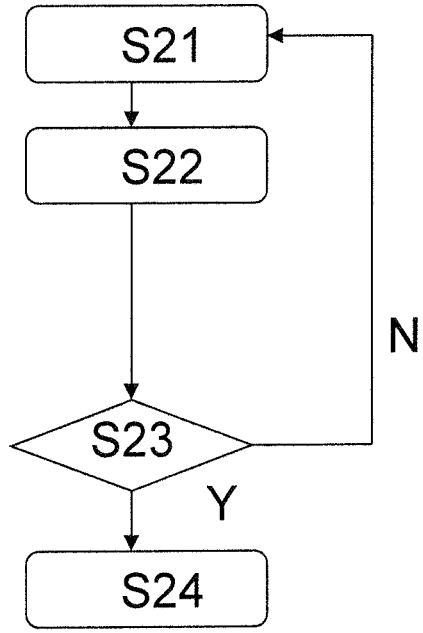

FIG. 41*a* represents a flow chart of an embodiment representing step S2 of FIG. 40 in more detail. In step S21 a first sound sample is selected to be played to the user. In step S22, the selected sound sample is played to the user, and in step S23 it is verified, if a user interface confirms (Y) the sound sample, or denies (N) the sound sample. In case the sound sample is denied (N) in step S23, a different sound sample is selected in step S21 and the process continues. The selection of sound samples may follow a defined sequence of sound samples, or may take user input into account, or even may include modification of existing sound samples according to the user input. In case the sound sample is confirmed (Y) in step S23, the frequency and/or loudness of the confirmed sound sample is handed over in step S24 to a process generating desired frequency characteristic, which may be represented by step S3 in FIG. 40.

Figure 41B:
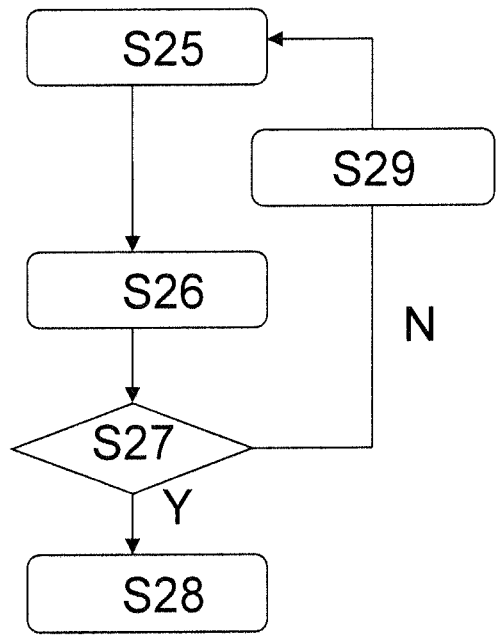

In an alternate process according to FIG. 41*b* representing step S2 of FIG. 33 in more detail, a basic sound sample is determined to be played to the user in step S25. In step S26, the basic sound sample is played to the user, and in step S27 it is verified, if a user interface confirms (Y) the sound sample, or denies (N) the sound sample. In case the sound sample is denied (N) in step S27, a setting to be applied to the basic sound sample is selected in step S29 and is applied to the basic sound sample in step S25 for generating a sound sample different from the basic sound sample. In case the sound sample is confirmed (Y) in step S27, the frequency and/or loudness of the confirmed sound sample is handed over to a process generating a desired frequency characteristic, which may be represented by step S3 in FIG. 40.

Figure 41C:
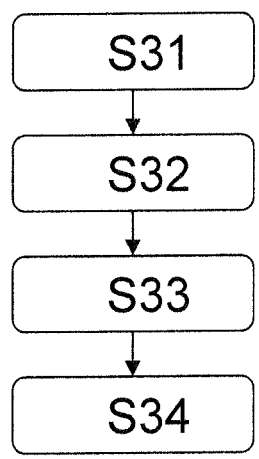

In FIG. 41*c*, the step S3 of FIG. 40 is explained in more detail. In this embodiment, the tinnitus suppression frequency and optionally one or more further quantities, such as tinnitus loudness, tinnitus deletion time and hearing threshold, is received in step S31. In step S32, a frequency characteristic is determined based on the received tinnitus suppression frequency and further quantities. In step S33, an audio signal is selected automatically, or in response to a user input. The audio signal may e.g. be a track of music stored in a memory of the electronic device, or a sound in the environment recorded by a microphone of the device. In step S34, the frequency characteristic is applied to the selected audio signal, and the audio signal adapted in this way is stored in the electronic device, if desired.

While there are shown and described presently preferred embodiments of the invention, it is to be distinctly understood that the invention is not limited thereto but may be otherwise variously embodied and practiced within the scope of the following claims.

The invention claimed is:

1. A device for providing an audio signal for suppressing or decreasing a user's tinnitus, comprising:
   an identification unit configured to support a determination of at least one parameter regarding the user's tinnitus;
   an adaptation unit configured to modify a received audio signal based on the at least one parameter, thereby obtaining the audio signal, or to generate the audio signal based on the at least one parameter, wherein a defined frequency spectrum of the audio signal is based on a tinnitus suppression frequency, and wherein the defined frequency spectrum comprises a narrow-bandwidth characteristic within half of an octave or within one fourth of an octave around the tinnitus suppression frequency and/or around a frequency one octave below the tinnitus suppression frequency; and an audio output unit configured to play the audio signal to the user, wherein the tinnitus suppression frequency is a tinnitus frequency, wherein the at least one parameter comprises the tinnitus suppression frequency, wherein the audio signal has the defined frequency spectrum comprising a peak of intensity with a peak frequency being one or more of:

at the tinnitus suppression frequency;

within a frequency range between one fourth of an octave below and one fourth of an octave above the tinnitus suppression frequency;

at a frequency one or more octaves below and/or above the tinnitus suppression frequency; and within a frequency range between one fourth of an octave below and one fourth of an octave above the frequency one or more octaves below and/or above the tinnitus suppression frequency;

wherein the audio signal is alternating or intermittent in time, and wherein the adaptation unit is configured to decrease a loudness of the audio signal over time continuously or stepwise.

2. The device according to claim 1, wherein the identification unit is configured to play sounds of different frequencies to the user, to prompt an input of the user in response to the sounds of different frequencies, and to determine the tinnitus suppression frequency by evaluating the input.

3. The device according to claim 1, wherein the at least one parameter comprises a minimum required loudness for the audio signal for suppressing or decreasing the user's tinnitus, wherein the identification unit is configured to support a determination of the minimum required loudness, wherein the identification unit is configured to play sounds of different loudness to the user, to prompt an input of the user dependent on the tinnitus being suppressed or not, and to determine the minimum required loudness by evaluating the input, and wherein the audio signal has a loudness equal to the minimum required loudness within a tolerance of 10% of a value of the loudness in dB.

4. The device according to claim 3, wherein the identification unit is configured to support a regular re-determination of the minimum required loudness, every week or month, and wherein the adaptation unit is configured to adapt the audio signal to the re-determined minimum required loudness.

5. The device according to claim 3, wherein the adaptation unit is configured to gradually lower the loudness of the audio signal over time starting from the minimum required loudness, wherein the identification unit is configured to accept a user input regarding a re-appearance of the tinnitus, and wherein the adaptation unit is configured to increase or decrease the loudness of the audio signal by a defined amount, which is in a range between 1 and 5 dB, in response to the user input.

6. The device according to claim 1, wherein the at least one parameter comprises an interval of tinnitus suppression, wherein the identification unit is configured to play a sound with the defined frequency spectrum to the user, to prompt an input of the user in response to the sound, and to determine the interval of tinnitus suppression by evaluating the input, wherein the interval of alternation or intermittency is synchronized with or shorter than the interval of tinnitus suppression.

7. The device according to claim 1, wherein the audio signal is a sinus signal, or is derived from a sinus signal, wherein the defined frequency spectrum has zero intensity for frequencies other than the peak frequency.

8. The device according to claim 1, wherein the alternating or intermitting audio signal comprises a steep slope between a first loudness and a second loudness, wherein a duration of the slope is below 0.5 s or is below 0.1 s, and the slope has a form of a step function.

9. The device according to claim 1, wherein the adaptation unit is configured to receive the audio signal from a database, and wherein the database is stored in a memory of the device.

10. The device according to claim 1, wherein the identification unit is configured to support a re-determination of the at least one parameter regarding the user's tinnitus, and wherein the adaptation unit is configured to adapt the audio signal to the re-determined at least one parameter, and wherein the identification unit is configured to initiate the re-determination after a regular time interval.

11. The device according to claim 1, wherein the identification unit is configured to accept a user input when the user input starts to perceive again the tinnitus, and wherein the identification unit is configured to re-determine the at least one parameter comprising the loudness of the audio signal, dependent on the user input.

12. A method for generating an audio signal or modifying a received audio signal to obtain the audio signal on an electronic device, comprising steps of:

supporting a determination of at least one parameter regarding a user's tinnitus;

modifying the received audio signal based on the at least one parameter, thereby obtaining the audio signal, or generating the audio signal based on the at least one parameter, wherein a defined frequency spectrum of the audio signal is based on a tinnitus suppression frequency, and wherein the defined frequency spectrum comprises a narrow-bandwidth characteristic within half of an octave or within one fourth of an octave around the tinnitus suppression frequency and/or around a frequency one octave below the tinnitus suppression frequency;

playing the audio signal to the user; and
decreasing a loudness of the audio signal over time continuously or stepwise;
wherein the audio signal has a defined frequency spectrum comprising a peak of intensity with a peak frequency being one or more of:
   at the tinnitus suppression frequency;
   within a frequency range between one fourth of an octave below and one fourth of an octave above the tinnitus suppression frequency;
   at a frequency one or more octaves below or above the tinnitus suppression frequency; and
   within a frequency range between one fourth of an octave below and one fourth of an octave above the frequency one or more octaves below or above the tinnitus suppression frequency;
wherein the tinnitus suppression frequency is a tinnitus frequency,
wherein the at least one parameter comprises the tinnitus suppression frequency, and
wherein the audio signal is alternating or intermittent in time.

13. The method according to claim 12,
wherein the received audio signal is modified according to the defined frequency spectrum based on the at least one parameter, or generating the audio signal according to the defined frequency spectrum based on the at least one parameter,
wherein the at least one parameter comprises one or more of the user's tinnitus suppression frequency, tinnitus loudness, minimum required loudness, interval of tinnitus suppression and hearing threshold.

14. A non-transitory computer readable medium having stored thereon a computer program comprising instructions which, when the program is executed by a hardware processor of an electronic device, cause the electronic device to carry out the steps of the method according to claim 12.

* * * * *